United States Patent
Seppänen et al.

(10) Patent No.: US 11,771,355 B2
(45) Date of Patent: Oct. 3, 2023

(54) METHODS AND APPARATUS FOR ANALYZING AND PROVIDING FEEDBACK OF TRAINING EFFECTS, PRIMARY EXERCISE BENEFITS, TRAINING STATUS, BALANCE BETWEEN TRAINING INTENSITIES AND AN AUTOMATIC FEEDBACK SYSTEM AND APPARATUS FOR GUIDING FUTURE TRAINING

(71) Applicant: Firstbeat Analytics Oy, Jyväskylä (FI)

(72) Inventors: Mikko Seppänen, Jyväskylä (FI); Johanna Toivonen, Jyväskylä (FI); Aki Pulkkinen, Jyväskylä (FI); Perttu Luukko, Jyväskylä (FI); Sami Saalasti, Jyväskylä (FI); Tero Myllymäki, Jyväskylä (FI); Veli-Pekka Kurunmaki, Jyväskylä (FI); Tuukka Ruhanen, Jyväskylä (FI)

(73) Assignee: Firstbeat Analytics Oy

( * ) Notice: Subject to any disclaimer, the term of this patent is extended or adjusted under 35 U.S.C. 154(b) by 706 days.

(21) Appl. No.: 16/794,279

(22) Filed: Feb. 19, 2020

(65) Prior Publication Data
US 2020/0261011 A1    Aug. 20, 2020

Related U.S. Application Data

(60) Provisional application No. 62/807,437, filed on Feb. 19, 2019.

(51) Int. Cl.
*A61B 5/22* (2006.01)
*A61B 5/024* (2006.01)
*G06Q 10/1093* (2023.01)
*G16H 20/30* (2018.01)
*A61B 5/0255* (2006.01)

(52) U.S. Cl.
CPC ............ *A61B 5/222* (2013.01); *A61B 5/0255* (2013.01); *A61B 5/02405* (2013.01); *G06Q 10/1097* (2013.01); *G16H 20/30* (2018.01)

(58) Field of Classification Search
CPC ... A61B 5/222; A61B 5/0255; A61B 5/02405; G16H 20/30; G06Q 10/1097
See application file for complete search history.

(56) References Cited

U.S. PATENT DOCUMENTS

| | | | |
|---|---|---|---|
| 7,192,401 B2 | 3/2007 | Saalasti | |
| 2013/0040272 A1* | 2/2013 | Booher | G16H 20/30 434/254 |
| 2014/0088444 A1* | 3/2014 | Saalasti | G16H 20/30 600/484 |
| 2017/0143262 A1* | 5/2017 | Kurunmäki | A61B 5/7264 |

* cited by examiner

*Primary Examiner* — Catherine M Voorhees
*Assistant Examiner* — Roland Dinga
(74) *Attorney, Agent, or Firm* — Samuel M. Korte; Max M. Ali

(57) ABSTRACT

A method, device and a computer program product for determining a training load distribution of a user is provided. Heart rate is continuously measured by a heart rate sensor. An aerobic training effect and load are calculated using intensity values and divided into categories of Aerobic Low and Aerobic High. An anaerobic training effect and load are calculated using determined characteristics related to high intensity periods of an exercise.

16 Claims, 25 Drawing Sheets

Fig. 7

Table 1. Short feedback phrases

| | Anaerobic TE | | | | | | | | |
|---|---|---|---|---|---|---|---|---|---|
| | 1.0 | 1.5 | 2.0 | 2.5 | 3.0 | 3.5 | 4.0 | 4.5 | 5.0 |
| No other conditions | No anaerobic effect | Minor anaerobic effect | Maintaining - Anaerobic base | | Improving - Anaerobic base | | Highly Improving - Anaerobic power & capacity | | Overreaching - Anaerobic power & capacity |
| High speed (modified intensity >140%VO2max) detected in 5 or more repeats | Very easy Fast force production | Easy - Fast force production | Maintaining - Fast force production | | Improving - Anaerobic capacity & Speed | | Highly Improving - Anaerobic capacity & Speed | | Overreaching - Anaerobic power & capacity |
| High intensity anaerobic exertion (modified intensity > 115% Vo2max) detected in 3 or more repeats | No anaerobic effect | Minor anaerobic effect | Maintaining - Anaerobic power | | Improving - Anaerobic power & capacity | | Highly Improving - Anaerobic power & capacity | | Overreaching - Anaerobic power & capacity |
| Moderate intensity anaerobic exertion (modified intensity > 100%VO2max) detected in 7 or more repeats | No anaerobic effect | Minor anaerobic effect | Maintaining - Anaerobic base & economy | | Improving - Anaerobic base & economy | | Highly Improving - Anaerobic base & economy | | Overreaching - Anaerobic power & capacity |

Table 2. Long feedback phrases

| | Anaerobic TE | | | | | | | | |
|---|---|---|---|---|---|---|---|---|---|
| | 1.0 | 1.5 | 2.0 | 2.5 | 3.0 | 3.5 | 4.0 | 4.5 | 5.0 |
| No other conditions | No anaerobic effect due to too little or lacking supramaximal work. | This exercise had a minor anaerobic benefit brought on by detected few anaerobic work periods. | This exercise maintained anaerobic base and anaerobic power production brought on by moderate amount of supramaximal exertion. | | This exercise improved anaerobic base and anaerobic power production brought on by high amount of supramaximal exertion. | | This exercise sharply improved anaerobic power production and anaerobic capacity brought on by very high amount of supramaximal exertion. | | This was a very hard anaerobic training session. This kind of exercise should be performed only occasionally. Special attention on recovery. |
| High speed (modified intensity >140%VO2max) detected in 5 or more repeats | This exercise had a minor effect on speed and fast force production capacity brought on by high speed/power of repeats. | This exercise had a minor effect on speed and fast force production capacity brought on by high speed/power of repeats. | This exercise had a significant effect on speed and fast force production capacity brought on by high speed/power of repeats. | | This exercise improved anaerobic capacity and speed brought on by high speed/power of repeats. | | This exercise sharply improved anaerobic capacity and speed brought on by high speed/power of repeats. | | This was a very hard anaerobic training session. This kind of exercise should be performed only occasionally. Special attention on recovery. |
| High intensity anaerobic exertion (modified intensity > 115% VO2max) detected in 3 or more repeats | No anaerobic effect due to too little or lacking supramaximal work. | This exercise had a minor anaerobic benefit brought on by detected few anaerobic work periods. | This exercise maintained anaerobic power production brought on by high intensity repeats | | This exercise improved anaerobic power production and capacity brought on by high intensity repeats | | This exercise sharply improved anaerobic power production and anaerobic capacity brought on by very high amount of supramaximal exertion. | | This was a very hard anaerobic training session. This kind of exercise should be performed only occasionally. Special attention on recovery. |
| Moderate intensity anaerobic exertion (modified intensity > 100%VO2max) detected in 7 or more repeats | No anaerobic effect due to too little or lacking supramaximal work. | This exercise had a minor anaerobic benefit brought on by detected few anaerobic work periods. | This exercise maintained anaerobic base and economy of movement brought on by moderate duration of anaerobic work periods. | | This exercise improved anaerobic base and economy of movement brought on by long duration of anaerobic work periods. | | This exercise sharply improved anaerobic base and economy of movement brought on by extensive duration of anaerobic work periods. | | This was a very hard anaerobic training session. This kind of exercise should be performed only occasionally. Special attention on recovery. |

| ANAEROBIC FEEDBACK PHRASE LOGIC | | | | | | | |
|---|---|---|---|---|---|---|---|
| | | Anaerobic TE | | | | | |
| | Other conditions | 0-0.9 | 1.0-1.9 | 2.0-2.9 | 3.0-3.9 | 4.0-4.9 | 5.0 |
| | | Only anaerobic phrases 0-4 and 15 are possible when "gym" flag is selected for a workout<br><br>Other rules related to use of ETE library:<br><br>Speed inputted to ETE only in running exercises. Power inputted to ETE only in cycling workouts | | | | | |
| Power | No other conditions | #0 | #15 | #1 | #2 | #3 | #4 |
| c1<br><br>Speed | Peak modified intensity >140% in 5 or more repeats (scale 12-17MET => 150%-130%) AND each repeat lasting 20sec or less | #0 | #5 | #6 | #12 | #13 | #4 |
| c2<br><br>Power | Average mod intensity > 115% for a total of 75 sec or more AND in 3 or more repeats AND each repeat lasting 10 sec or more (scale 12-17MET => 120%-110%) | #0 | #15 | #7 | #8 | #3 | #4 |
| c3<br><br>Power | Average mod intensity > 95% for a total of 150 sec or more AND in 7 or more repeats (scale 12-17MET => 100%-95%) AND each repeat lasting 20sec or more AND aerTE < 4.0 | #0 | #15 | #10 | #11 | #14 | #4 |

Fig. 17

| AEROBIC FEEDBACK PHRASE LOGIC | | | | | | | | | | |
|---|---|---|---|---|---|---|---|---|---|---|
| | | Aerobic TE | | | | | | | | |
| | Other conditions | 0-0.9 | 1 | 1.5 | 2 | 2.5 | 3 | 3.5 | 4 | 4.5 | 5 |
| Recovery/ Tempo | No other conditions | #18 | #0 | | #1 | | #2 | | #3 | | #4 |
| c1: Recovery/ Tempo | 10min ≤ Duration ≤ 40min AND anTE < 1,0 | #18 | #5 | | #1 | | #2 | | #3 | | #4 |
| c2: Recovery/ Base | Duration > 40min AND Time in HR zone > 95%LTHR for less than 8% of total duration AND C4t2+C5t2 less than 15% of total duration AND anTE <4.0 AND time at 61-92% LTHR > 35min | #18 | #0 | #6 | #7 | #8 | #9 | | #10 | | #11 |
| c3: Recovery/ Tempo | Cumulative time<br>1. @ HR zone 90-96%LTHR equal to or more than 18-24min AND cumulative time equal to or more than 20% of total exercise time<br>2. OR ETEspeed @ 90-96% of AnT speed ≥ 18-24 min AND cumulative time equal to or more than 22% of total exercise time<br>3. OR 30sec_avg_power @ 76-92% of Antpower) ≥ 24-32 min AND "interval not detected " AND cumulative time equal to or more than 25% of total exercise time<br><br>AND anTE < 4.0 | #18 | #0 | | #21 | | #22 | | #23 | | #24 |
| c4: Recovery/ LT | Cumulative time<br>1. @ 94-102% LTHR AND @ modified intensity < 95% VO2max equal to or more than 10-15 min AND cumulative time equal to or more than 15% of total exercise time<br>OR<br>2. @ ETEspeed 94-105% of AnT speed equal to or more than 10-15min AND cumulative time equal to or more than 15% of total exercise time<br>OR<br>3. @ 30sec_avg_power 90-105% of AnT power equal to or more than 13-18 min AND "interval not detected " AND cumulative time equal to or more than 20 % of total exercise time<br><br>AND anTE < 4.0 | #18 | #0 | | #19 | | #12 | | #13 | | #14 |
| c5: Recovery/ VO2max | If duration ≥ 5min AND cumulative time at one of the zones (see below; either based on % LTHR or %ETEspeed or %AnT power) in zone greater than 8 min or more than 80% of total duration<br><br>else if..<br><br>Cumulative time<br>1. @ ≥ 100% LTHR AND modified intensity ≤ 103% equal to or more than 8-12 min<br>OR<br>2. @ ETEspeed ≥ 102% of AnT speed AND modified intensity ≤ 103% equal to or more than 8-12min min AND cumulative time equal to or more than 10% of total exercise time<br>OR<br>3. @ 30sec_avg_power higher than 102% of AnT power AND smaller than 127% of AnT power equal to or more than 8-12 min AND "interval not detected "<br><br>AND cumulative time equal to or more than 15% of total exercise time | #18 | #0 | | #20 | | #15 | | #16 | | #17 |

Fig. 18

| ANAEROBIC FEEDBACK PHRASES ||||
|---|---|---|---|
| Feedback phrase number | Workout label | Short TE Feedback | Long TE Feedback |
| #0 | NaN | No anaerobic effect | No anaerobic effect due to too little or lacking supramaximal work |
| #1 | #6 Anaerobic capacity | Maintaining Anaerobic Fitness | This exercise maintained anaerobic performance brought on by moderate amount of supramaximal exertion. |
| #2 | #6 Anaerobic capacity | Improving Anaerobic Fitness | This exercise improved anaerobic performance brought on by high amount of supramaximal exertion. |
| #3 | #6 Anaerobic capacity | Highly Improving Anaerobic Fitness | This exercise was very efficient for improving anaerobic power production and anaerobic capacity brought on by extensive amount of supramaximal exertion. |
| #4 | #6 Anaerobic capacity | Overreaching | This was a very hard anaerobic training session. This kind of exercise should be performed only occasionally. Special attention on recovery. |
| #5 | #7 Speed | Easy - Speed | This exercise had a good effect on speed and fast force production capacity brought on by high speed/power of repeats. |
| #6 | #7 Speed | Maintaining - Speed | This exercise had a significant effect on speed and fast force production capacity brought on by high speed/power repeats. |
| #7 | #6 Anaerobic capacity | Maintaining - Anaerobic power | This exercise maintained anaerobic power production capability brought on by high intensity repeats |
| #8 | #6 Anaerobic capacity | Improving - Anaerobic power & capacity | This exercise improved anaerobic power production and anaerobic capacity brought on by high intensity repeats |
| #9 | #7 Speed | Very easy - Speed | This exercise had a minor effect on speed and fast force production capacity brought on by high speed/power repeats. |
| #10 | #6 Anaerobic capacity | Maintaining - Anaerobic base & economy | This exercise maintained anaerobic base and economy of movement brought on by moderate duration of anaerobic work periods. |
| #11 | #6 Anaerobic capacity | Improving - Anaerobic base & economy | This exercise improved anaerobic base and economy of movement brought on by long duration of anaerobic work periods. |
| #12 | #7 Speed | Improving - Anaerobic capacity & Speed | This exercise improved anaerobic capacity and speed brought on by high speed/power of repeats. |
| #13 | #7 Speed | Highly Improving - Anaerobic capacity & Speed | This exercise sharply improved anaerobic capacity and speed brought on by high speed/power of repeats. |
| #14 | #6 Anaerobic capacity | Highly Improving - Anaerobic base & economy | This exercise sharply improved anaerobic base and economy of movement brought on by extensive duration of anaerobic work periods. |
| #15 | #6 Anaerobic capacity | Minor anaerobic effect | This exercise had a minor anaerobic benefit brought on by detected few anaerobic work periods. |
| #16 | #7 Speed | Overreaching - Speed | This activity was very demanding. While it can significantly improve your anaerobic capacity, power and speed, it can become harmful without enough recovery time and should be done sparingly. |

Fig. 20

| AEROBIC FEEDBACK PHRASES ||||
|---|---|---|---|
| Feedback phrase number | Workout label | Short TE Feedback | Long TE Feedback |
| #0 | #1Recovery | Easy - aerobic | This was an easy aerobic exercise that had only a minor effect on your cardiorespiratory fitness. |
| #1 | #2Aerobic base | Maintaining - aerobic | This aerobic exercise session maintained your cardiorespiratory fitness. |
| #2 | #3Tempo | Improving - aerobic | This aerobic exercise session was hard enough for purposes of improving cardiorespiratory fitness. |
| #3 | #3Tempo | Highly improving - aerobic | This aerobic exercise session was very hard and is expected to cause sharp increase in cardiorespiratory fitness. |
| #4 | #3Tempo | Overreaching- aerobic | This aerobic exercise was very demanding for your body and fitness benefits occur only after prolonged recovery. These type of exercises should only be performed occasionally. |
| #5 | #1Recovery | Easy - recovery | This was an easy aerobic exercise. These type of exercises facilitate your recovery after harder training and helps in relieving mental stress. |
| #6 | #2Aerobic base | Easy - Aerobic base | This was an easy aerobic exercise. It had minor benefits for your aerobic base. |
| #7 | #2Aerobic base | Maintaining - aerobic base | Intensity and duration of this workout were high enough to maintain your aerobic base. |
| #8 | #2Aerobic base | Improving - aerobic base | This was a good exercise for improving aerobic base. These type of exercises together with easier aerobic base exercises form the basis of good training plan. |
| #9 | #2Aerobic base | Improving - aerobic endurance | This exercise improved your aerobic base as well as capability to endure exertion for prolonged periods. |
| #10 | #2Aerobic base | Highly improving - aerobic endurance | This exercise was very efficient in improving your aerobic base and capability to endure prolonged exertion. |
| #11 | #2Aerobic base | Overreaching - aerobic endurance | This was a very demanding exercise requiring long recovery. This exercise mainly improved your capability to endure prolonged exertion. |
| #12 | #4Lactate Threshold | Improving - lactate threshold | This was a good exercise for improving your lactate threshold! |

Fig. 21a

| \multicolumn{4}{c}{AEROBIC FEEDBACK PHRASES} |
| --- | --- | --- | --- |
| Feedback phrase number | Workout label | Short TE Feedback | Long TE Feedback |
| #13 | #4Lactate Threshold | Highly improving - lactate threshold | This exercise was very efficient in improving your lactate threshold! |
| #14 | #4Lactate Threshold | Overreaching - lactate threshold | This was a very demanding exercise requiring long recovery. Main physiological benefit in lactate threshold improvement. |
| #15 | #5VO2max | Improving - VO2max | This was a good exercise for improving your VO2max! |
| #16 | #5VO2max | Highly improving - VO2max | This exercise was very efficient in improving your VO2max! |
| #17 | #5VO2max | Overreaching - VO2max | This was a very demanding exercise requiring long recovery. Main physiological benefit in VO2max improvement. |
| #18 | NaN | No aerobic effect | This exercise did not provide any benefit for cardiorespiratory fitness. |
| #19 | #4Lactate Threshold | Maintaining - Lactate threshold | This exercise included enough high intensity effort to maintain your Lactate Threshold. |
| #20 | #5VO2max | Maintaining - VO2max | This exercise included enough high intensity effort to maintain your VO2max. |
| #21 | #2Tempo | Maintaining - Tempo | This exercise included some high intensity effort at [Marathon pace (running) OR Tempo zone (cycling)]. This type of effort level can be used to develop muscular endurance when performed a bit longer or using shorter recovery periods between intervals. |
| #22 | #2Tempo | Improving - Tempo | This exercise included enough high intensity effort at [Marathon pace (running) OR Tempo zone (cycling)] to improve your muscular endurance. |
| #23 | #2Tempo | Highly improving - Tempo | This was a really good exercise for developing muscular endurance. |
| #24 | #2Tempo | Overreaching - Tempo | This was a really demanding exercise and very efficient for developing muscular endurance. |

Fig. 21b

|         | MTL limit |
|---------|-----------|
| AC0.0   | 0         |
| AC1.0   | 17        |
| AC2.0   | 40        |
| AC3.0   | 68        |
| AC4.0   | 400       |
| AC5.0   | 548       |
| AC6.0   | 704       |
| AC7.0   | 876       |
| AC7.5   | 1092      |
| AC8.0   | 1336      |
| AC8.5   | 1731      |
| AC9.0   | 2177      |
| AC9.5   | 2792      |
| AC10.0  | 3512      |

Fig. 25

METHODS AND APPARATUS FOR ANALYZING AND PROVIDING FEEDBACK OF TRAINING EFFECTS, PRIMARY EXERCISE BENEFITS, TRAINING STATUS, BALANCE BETWEEN TRAINING INTENSITIES AND AN AUTOMATIC FEEDBACK SYSTEM AND APPARATUS FOR GUIDING FUTURE TRAINING

PRIORITY

This application claims priority of the U.S. provisional application No. 62/807,437 filed on Feb. 19, 2019, the contents of which are incorporated by reference.

FIELD OF THE INVENTION

These methods and apparatus relate to improved recognition of anaerobic sections of exercise and to providing feedback on training load or training effect reflecting energy systems used and trained during exercise.

BACKGROUND OF THE INVENTION

Energy for athletic training and exercising of an individual human may originate from anaerobic and aerobic sources. The anaerobic energy is produced when the production of energy from oxygen is not fast enough to meet the demands of external work. The substrates of anaerobic energy systems include energy from Adenosine Triphosphate (ATP) in muscles, Creatine Phosphate (PCr) resources, and muscle glycogen. Lactic acid is produced as the end product of anaerobic metabolism, but lactic acid can be further oxidized to yield ATP or resynthesized in liver to glycogen. The substrates of aerobic energy systems include muscle glycogen and circulating glucose and fatty acids. The key determinants of energy production are exercise intensity and time related.

Traditionally, aerobic and anaerobic parts of a specific exercise have been differentiated by heart rate training zones, for example so that heart rate over 90% of individual maximal heart rate has been categorized as anaerobic and under 90% as aerobic training. In more sophisticated solutions, this limit may have been defined by individual anaerobic threshold. However, these solutions lack deep understanding of the relationship between heart rate responses and external work performed and of the physiological responses eliciting training adaptations. Physiologically, when exercise intensity is quickly increased resulting in a need to use anaerobic energy pathways, there can be a mismatch between heart rate and metabolic responses, which need to be considered in order to evaluate anaerobic contributions to energy production and to assess training load accurately.

We present a method and system which relates to recognizing anaerobic parts of exercise from plurality of physiological and physical parameters. These parameters may contain information on physiological responses to exercise and may include heart rate, oxygen consumption, respiration rate, EPOC, TRIMP of which all may be analyzed from heartbeat data. Physical parameters may be external work such as speed, acceleration, power, and also theoretical work (theoretical oxygen consumption) performed. The system can recognize and differentiate anaerobic and aerobic sections from any type of exercise performed without specific exercise protocol (i.e. exercise can be freely performed), provide feedback of characteristics of different exercise sections (intervals), and training load contributing specifically to anaerobic and aerobic performance and energy systems. A method is also presented for estimation of anaerobic training effect. There are no means for estimation of training effect in prior art in supramaximal exercises or exercise where submaximal and supramaximal phases alternate. Only the estimation of training effect in submaximal exercises has been disclosed (applicants own patent U.S. Pat. No. 7,192,401). Since supramaximal training have been found effective in health enhancing purposes and fitness training, it is important to be able to estimate anaerobic training effects too. In addition, in many anaerobic type sports—such as soccer, ice-hockey, alpine skiing etc.—anaerobic training effect may be even more important than aerobic (cardiorespiratory) training effect considering development of physical capacities. Therefore, the invention helps athletes (exercisers) and/or personal trainers and coaches (all users of the invention) to assess more accurately the effects of training, which is crucial for optimizing the content of training from sports-specificity and individuality point of views. In addition, the described invention enables recognition of intervals and estimation of anaerobic training effect in real time. Accordingly, the invention helps in optimizing training dose for athletes or keep fit enthusiasts since coaches and or personal trainers (or exercisers themselves) are able to evaluate whether to continue exercise as planned or whether to increase or decrease intensity. The user can see in real-time the accumulated training load and the impact of training on energy production systems which are intimately related to training adaptations. Considering the analysis of past exercise, it is also useful for the exerciser or coach or trainer to know the number of intervals performed during exercise. In addition, information on the number and intensity of intervals as well as duration of recovery phases together with—or separate from—anaerobic training effect assessment support analysis of physiological training effects.

SUMMARY OF THE INVENTION

The invention aims is a method and an apparatus recognize of anaerobic sections of exercise and to provide feedback on training load or training effect reflecting energy systems used and trained during exercise.

The characteristic features of the method according to the invention and the features of the apparatus implementing the method are stated in the accompanying claims. The method according to the invention determines an 'oxygen debt' like cumulative physiological sum (usually training effect TE as EPOC value) brought on by a change in a body homeostasis and its aerobic and anaerobic values. Particularly anaerobic value may be determined by a procedure, where a total EPOC (or TRIMP) is determined as a total sum and an aerobic part calculated in a known manner, is deducted from the total sum. There are two main lines for implementing the invention. The first one scans high intensity phases and recognizes characteristics of each intervals therein using buffering and calculating probabilities to classify intervals. Another implementation uses a different approach, where a starting edge and a starting level of heart rate are main variables to achieve multiplication factor, which converts the measured intensity (% VO2 max) to the anaerobic intensity. That gives a value for a positive accumulation of anaerobic 'oxygen debt'. A recovery component and scaling may be used to obtain fully repeating results.

Exemplary disclosures of the embodiment may detect exercise intervals, analyze anaerobic exercise periods, analyze training effects and further provide feedback.

In one exemplary embodiment, a heart rate-based method and system for recognizing anaerobic sections of exercise and to providing feedback on training load or training effect reflecting energy systems and properties used and trained during an exercise may be conducted according to the following exemplary steps:

a) A user may start to exercise;

b) Heart rate and/or other physiological response of a user may be continuously measured by plurality of physiological parameters, and measured value or values may be recorded with time stamp as physiological data. Physiological parameters may include heart rate. Unreliable data points, such as ectopic beats of heart rate may be filtered or corrected by signal processing first, and remaining points may form accepted data points;

c) Recognition of high intensity intervals based on periods of increasing or decreasing physiological values, for example heart rate. High intensity intervals may be detected by analyzing the derivatives of heart rate with regard to time, i.e. the degree of heart rate changes. This may be done by using a data buffer for storing and analyzing information about the derivatives in real time; The characteristics of each interval are recorded into a buffer. These comprise at least starting % HRmax or % VO2 max-value, final peak % HRmax or % VO2 max-value and a value depicting the end of the interval as well as timestamps of these parameters The size of the buffer may be 16 records (generally 10-30), which means 80 s duration when 5 s frequency is used in calculation.

d) The probability of the period (interval) to be anaerobic section may be calculated based on the magnitude of the derivatives, heart rate differences, duration of the period, and heart rate level;

e) The found period can thereafter be rejected not to accumulate anaerobic units with specific rules that may be related to
   1) the time difference to the previous anaerobic period being too short if the heart rate level is higher than a certain threshold, for example 70% of HRmax, when the heart rate starts to increase,
   2) the highest heart rate during the period being lower than certain threshold, for example 80% of HRmax,
   3) the duration of the period being shorter than certain threshold, for example 15 seconds,
   4) the highest oxygen consumption value during the period being lower than a certain threshold, for example 73% of VO2 max, and
   5) the heart rate difference between the start of the period and the last local heart rate peak value at the end of the period being lower than a predetermined threshold value. The predetermined threshold value (=smallest allowable difference) may be proportional to the HRpeak;

f) Determining the anaerobic sum for the detected periods (high intensity intervals)

g) The anaerobic sum within specified exercise periods (high intensity intervals) that are accepted may be determined based on different factors that can be for example duration of the interval, the peak intensity of the interval as for example % VO2 max or % HRmax, the duration of peak intensity of interval, and the physiological recovery status immediately before the interval as % HRmax level of the person. The calculated anaerobic sum may be higher when the interval is shorter, the intensity is higher, and when the person's recovery status before the interval is better, i.e. heart rate is lower;

h) The periods (intervals) can be thereafter also categorized into different groups, for example but not limited to "clear anaerobic", "weak anaerobic", "long" based on quantification of anaerobic sum and duration of the period;

i) Characteristics of different exercise periods can be presented to the user, for example average duration and intensity of intervals.

j) Determining the anaerobic sum performed during steady-state high-intensity periods (=non-interval periods with high intensity) where the anaerobic sum may be cumulative in nature: For example during high exercise intensities, which may be for example 90-100% of HRmax, certain amount of anaerobic sum is cumulatively achieved. It may be related to exercise intensity so that the higher the intensity (i.e. the closer the person is his/her maximal heart rate) the higher anaerobic sum is achieved;

k) Defining the total anaerobic sum for the whole exercise period where the total anaerobic sum by putting together short high intensity intervals and non-interval periods with high intensity;

l) The total amount of anaerobic sum can thereafter be classified by comparing the sum with an anaerobic work scale. For example, a classification may comprise an anaerobic training effect having values between 1-5, and having a verbal description between very easy and very hard (overreaching) anaerobic exercise. Classification may be based on commonly known coaching science, i.e. anaerobic work quantities in different exercises. In addition, physical fitness level of a person may be taken into account when evaluating the anaerobic load of the performed exercise. In principle, a person with higher fitness level (or activity level) needs to get higher anaerobic sum to achieve similar training effect;

m) In similar fashion, the performed aerobic sum is scaled during exercise by comparing measured aerobic sum to reference values for aerobic work. Aerobic sum may be measured with physiological parameters, for example using EPOC and/or TRIMP that are calculated based on heartbeat data. Person's physical fitness level may be taken into account when classifying the calculated aerobic sum. Classification of aerobic sum may comprise aerobic training effect having values typically between 1 and 5, and having a verbal description between minor and overreaching training effect.

n) Further, the proportion of anaerobic effect can be continuously calculated by comparing aerobic and anaerobic training effect–values Scaling of Aerobic and Anaerobic Training Effects
1=Minor training effect/very easy
2=Maintaining training effect/easy
3=Improving training effect/moderate or somewhat hard
4=Highly improving training effect/hard
5=Overreaching training effect/very hard Following equation (1) may be used to assess the proportion of aerobic and anaerobic training effect (TEaer and TEanaer, respectively) from the overall training effect if both values are under training effect value 5 (Overreaching).

$$proportion of anaerobic effect = \frac{TEanaer}{TEanaer + TEaer}. \quad (1)$$

If calculated anaerobic sum is higher than required for anaerobic Training effect value 5 (Overreaching), TEanaer can be replaced in the formula by the following equation:

$$TEanaer = \frac{anaerobicSum}{anaerobicSumatTE5level}, \quad (2)$$

in which anaerobic sum at TE5 level is the sum required to achieve Training Effect value 5 (Overreaching). In a similar fashion, if the aerobic sum defined by EPOC and/or TRIMP is higher than required aerobic sum for Training Effect value 5, TEaer can be replaced in the formula by the following equation:

$$TEaer = \frac{aerobicSum}{aerobicSumatTE5level}. \quad (3)$$

One exemplary embodiment comprising speed/altitude or power measurement comprises the following steps:
1. Heart rate and external work output (speed+altitude or power output) are measured during a user performed exercise session
2. Modified intensity (=theoretical VO2) can be calculated using weighted average of heart rate and external workload. External workload can be determined using either the combination of speed and altitude, or power output alone. The resulting value (e.g. ml/kg/min) may be divided by person's maximal oxygen uptake to get proportional intensity (% VO2 max) estimate.
   a. It is also possible to calculate modified intensity solely based on external workload. However, combining information on external workload with heart rate in formation may significantly stabilize modified intensity value.
3. Proportional intensity (% VO2 max) estimate is calculated based on heart beat data.
4. EPOC value is pre-predicted during the exercise using the % VO2 max estimate derived from modified intensity
5. EPOC value is pre-predicted during the exercise using the % VO2 max estimate derived from heart beat data
6. Calculating continuously two different Training Effect (TE) estimates based on two different EPOC values
7. Selecting the higher Training Effect value to represent the total Training effect of the exercise or presenting both TE values simultaneously to the user
8. If willing to provide aerobic and anaerobic TE contribution to a user, dividing HR based EPOC estimate by the EPOC estimate derived from work output. Alternatively, HR based TE can be divided by Total TE.

Any of the calculated parameters can be given during and/or after exercise to the user, or to any external system.

In an exemplary embodiment, labels may be applied to each training workout to provide additional feedback. Feedback phrase logic is based on determined anaerobic and aerobic training effect (anTE and aerTE, respectively) in addition to other workout criteria. A workout label gives a description of the impacts of training session, covering both aerobic and anaerobic training.

Workout labels are based on aerobic and anaerobic feedback phrases—each feedback phrase has a corresponding workout label. Each workout accumulates both aerobic and anaerobic load if both aerTE and anTE are 1.0 or greater. Determined aerobic training load is transferred to a selected aerobic label and anaerobic training load is transferred to a selected anaerobic label. Based on the cumulative training load sum for both anaerobic and aerobic training load, and the identified workout label, the respective training load units are transferred to the particular label. Over multiple workouts, training load units can accumulate within specific labels and identify the proportion of the types of training over a given period.

Workout labels are then also used to analyze the distribution of training load. The distribution of training load may be displayed using the associated labels, and can also be simplified further into coherent intensity categories that generally describe the energy systems being used. Distribution of training load is based on training loads collected over a month's time or extrapolated to represent approximately a month.

The method could be implemented in any device comprising a processor, memory and software stored therein and a user interface, for example, a heart rate monitor, fitness device, mobile phone, PDA device, wristop computer, personal computer, and the like.

BRIEF DESCRIPTION OF THE FIGURES

Advantages of embodiments of the present disclosure will be apparent from the following detailed description of the exemplary embodiments. The following detailed description should be considered in conjunction with the accompanying figures in which:

Figure 7:
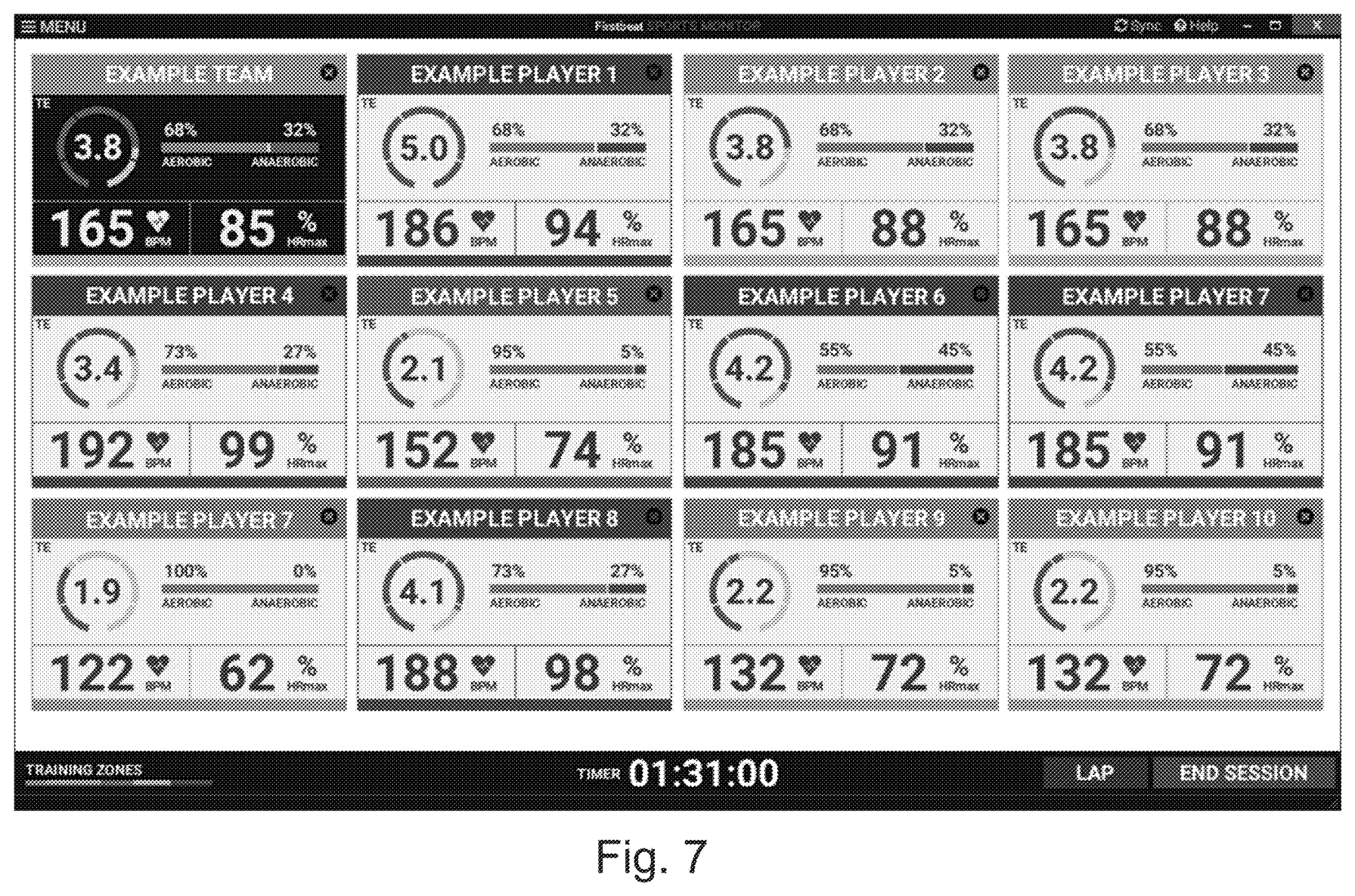

FIG. 7 represents an example of user interface with a real time group view wherein the contribution of aerobic and anaerobic training effects, the total training effect, and current exertion level of several athletes is shown on a single display.

FIG. 15 presents "Table 1 Short feedback phrases"

FIG. 16 presents "Table 2 Long feedback phrases"

FIG. 17 presents an example table of an alternative embodiment for the selection of anaerobic feedback FIG. 18 presents an example table of an alternative embodiment for the selection of aerobic feedback FIG. 20 represents example anaerobic feedback phrase, both "short" and "long" phrases.

FIGS. 21*a* and 21*b* represent example aerobic feedback phrases.

FIG. 25 shows a table with sample monthly training load limits based on activity class.

Figure 1:
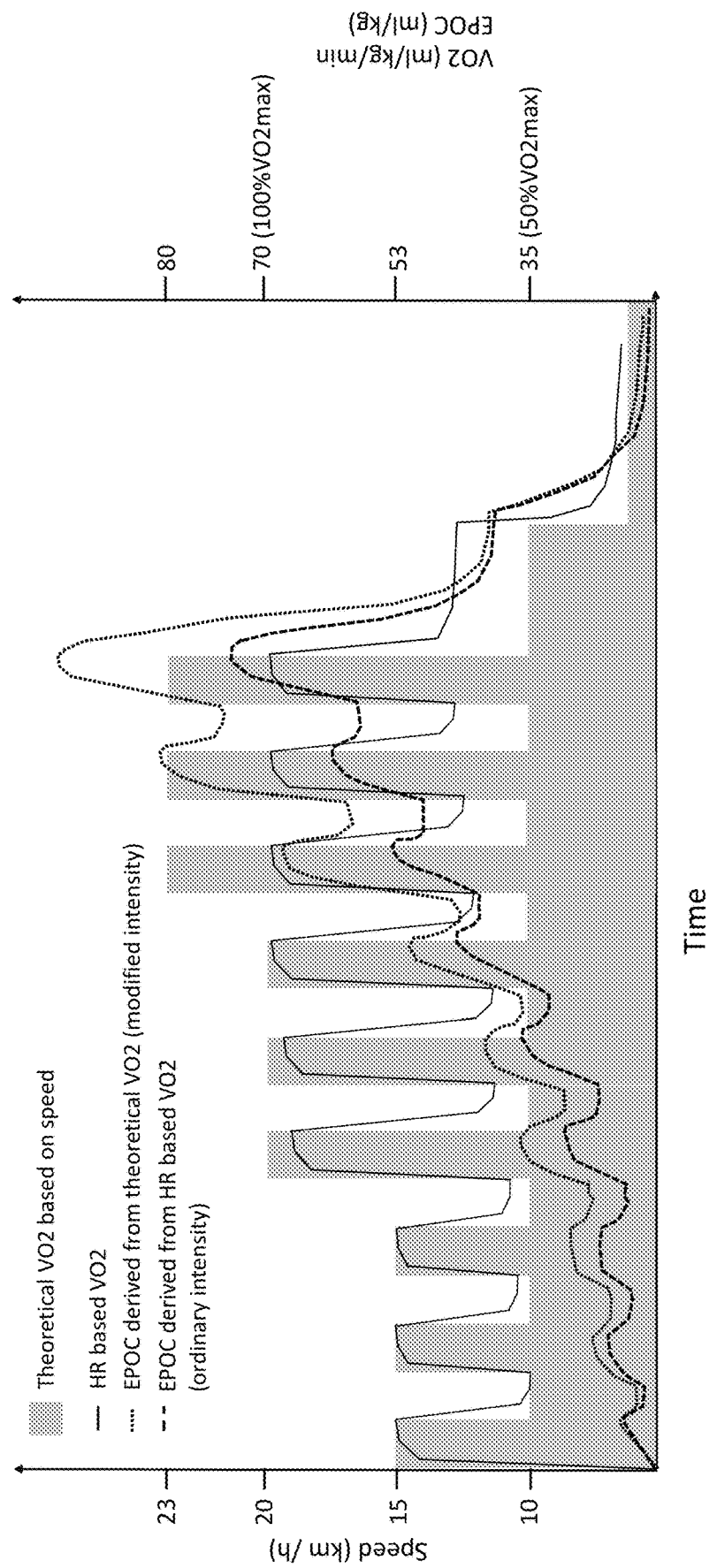
FIG. 1 represents a sprint interval exercise where external workload based EPOC (=modified intensity based EPOC; modified intensity can be calculated also solely based on heart rate information) accumulates to a significantly higher level than HR based EPOC. Training session has improving anaerobic training effect.

The Figures may show exemplary embodiments of the system, method, computer product, and apparatus for detecting exercise intervals, analyzing anaerobic exercise periods, and analyzing individual training effects as herein described. Figures are only exemplary, and they cannot be regarded as limiting the scope of invention.

DETAILED DESCRIPTION

The following table shows some exemplary definitions and abbreviations of terms used in the exemplary embodiments described herein.

| Term or abbreviation | Definition |
| --- | --- |
| Anaerobic Training Effect | The physiological impact or effect the training has on anaerobic performance calculated by analyzing the anaerobic sum (e.g. analyzing high-intensity intervals) and by scaling that based on commonly known quantities of anaerobic work in different exercises. |
| Anaerobic sum | The physiological stimulus caused by the anaerobic work performed during exercise. Anaerobic sum is calculated by detecting anaerobic sections and continuous high-intensity work from exercise |
| High intensity interval | A period of continuous work during an exercise having typically higher intensity than during rest or recovery periods within exercise. An intermittent (interval-type) exercise typically includes two or more intervals. |
| Clear anaerobic interval | An anaerobic high intensity interval with a higher anaerobic sum than a certain threshold value |
| Weak anaerobic interval | An anaerobic interval with a lower anaerobic sum than a threshold value that is required for a clear anaerobic interval |
| Long interval | An interval that is longer than a certain threshold value, e.g. 200 seconds |
| Aerobic Training Effect | The physiological impact or effect the training has on aerobic performance calculated by analyzing the aerobic sum performed (e.g. using EPOC, TRIMP) and scaling the sum based on commonly known quantities of aerobic work in different exercises |
| Aerobic sum | The physiological stimulus caused by aerobic work performed during exercise and calculated by assessing EPOC and/or TRIMP during exercise |
| Anaerobic threshold = AnT | Anaerobic threshold refers to the highest velocity or external power output that a person's can maintain during physical activity without continuous lactic acid accumulation. AnT can be determined automatically during a user performed high intensity exercise where heart beat interval data and external workload are measured. |

-continued

| Term or abbreviation | Definition |
|---|---|
| HR | Heart rate (beats/min) |
| HRmax | maximum heart rate (of a person) (beats/min) |
| ΔHR | Change of heart rate level |
| % HRmax | heart rate relative to maximum heart rate |
| VO2 | Oxygen consumption (ml/kg/min) |
| VO2max | maximum oxygen consumption capacity of a person (ml/kg/min) that reflects cardiorespiratory fitness level of the person |
| % VO2max | measured or estimated VO2 relative to VO2max of a person - may be calculated using either HR level information or HRV information |
| RespR | Respiration rate that can be derived e.g. based on heart rate variability measures |
| Theoretical VO2 or theoretical oxygen consumption | Value that describes external workload (ml/kg/min). Can be calculated based on speed and altitude change (or speed and grade of inclination), or based on measured power output in bicycles and other exercise equipment or measured power output during running. |
| on/off - kinetics information | Information related to heart beat data that reflects the rate of change in HR based VO2 estimate |
| Δt | Refers to instant time or change in time OR duration |
| Activity level/activity class (AC) | Refers to person's physical activity level and how much the person is used to exercise. For example, has an effect for following: How much exercise can be tolerated by the person without overstraining one's body OR what is the quantity of exercise that is needed achieve a given training effect. |
| METmax/maxMET/maximal_MET | maximum oxygen uptake capacity of a person relative to resting oxygen consumption = VO2max (ml/kg/min)/resting VO2 (ml/kg/min) = VO2max (ml/kg/min)/3.5 ml/kg/min |
| Modified intensity | Intensity estimate that depicts true oxygen requirement during exercise as ml/kg/min or METs or with respect to VO2max (% VO2max). Modified intensity can be calculated using a combination of external workload and heart rate or using only either one of them alone. |
| R-R-interval = RRI | Time interval between successive heart beats in ECG-signal that is measured using e.g. a heart rate monitor. Analysis of R-R intervals (=heart rate variability) allows assessment of e.g. respiration rate in addition to heart rate.<br>Measurement of RRI is not mandatory for applying the methods described in this document. Beat-to-beat signal derived from e.g. PPG-signal can be used as well. In addition, all methods can be applied also using heart rate level information from either ECG or PPG signal. |
| HRV | Heart rate variability meaning the variation in time interval between successive heart beats. The magnitude of heart rate variability may be calculated from electrocardiographic or photoplethysmographic signals, for example. |
| Freely performed physical exercise | An exercise that may be performed without a specific protocol.<br>The user may freely decide the intensity of exercise, as well as recovery periods inside the exercise session. |
| Continuous measurement | Heart beats may be recorded beat-by-beat or 1-15 sec intervals and external power with similar 0.1-15 sec intervals. Calculation of results may be performed with 1-15 sec intervals where 1-5 sec frequency may enable better accuracy. (Selected number of values are recorded) |
| Training load | A measure of accumulated load caused by training. The higher the training load the higher is also training stimulus. EPOC and TRIMP are typically used measures of training load. |
| TRIMP (Training impulse) | A cumulative measure describing training load. TRIMP is merely a mathematical index, not a physiological measure |
| EPOC (Excess post-exercise oxygen consumption) | EPOC reflects the extent of disturbance in body's homeostasis brought on by exercise. As it can be nowadays estimated or predicted - based on heart rate or other intensity derivable parameter - it can be used as a cumulative measure of training load in athletic training and physical activity. |

-continued

| Term or abbreviation | Definition |
| --- | --- |
| Non-interval period | Time during exercise that is either recovery phase (or low intensity phase) between high intensity intervals OR high intensity exercising period that cannot be regarded as interval training. |
| Workout labels | Workout labels give a simple description of the impacts of training session and it covers both aerobic and anaerobic training. Workout labels are based on aerobic and anaerobic feedback phrases - each feedback phrase has a corresponding workout label (see FIG. 19). Each workout may accumulate both aerobic and anaerobic load if both aerobic TE, and anaerobic TE are 1.0 or greater. Aerobic load is transferred to selected aerobic label and anaerobic load is transferred to selected anaerobic label. E.g. if workout's aerobic load // label are = 75 // #2 and anaerobic load // label = 25 // #7; then 75 units of aerobic load in transferred to aerobic base-label and 25 units of load to speed-label. |
| Training load distribution | Workout labels are used to analyze training load distribution. While "time in zone analysis" over week(s) has been possible already, labels provide benefits over time in zone approach as they help to differentiate between well-structured training from poorly planned training. For example, traditional "time in zone" analysis may have a good distribution of intensities in long term analysis even if a person performs high intensity interval training each time he/she exercises since time at low aerobic intensities accumulate during warm-ups and cool downs. No major changes would be recommended to future training. However, applicant's present invention would reveal the excess amount of high intensity training and that the person should perform more low intensity workouts in the future to maintain balance in the development of body's energy systems. Additionally, traditional heart rate based intensity zone model does not and cannot provide any information on accumulated time or effort at supramaximal intensities thus excluding different kind of anaerobic training (speed endurance and pure speed) from the overall training load distribution. |

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Further, many of the embodiments described herein are described in terms of sequences of actions to be performed by, for example, elements of a computing device. It should be recognized by those skilled in the art that the various sequences of actions described herein can be performed by specific circuits (e.g. application specific integrated circuits (ASICs)) and/or by program instructions executed by at least one processor. Additionally, the sequence of actions described herein can be embodied entirely within any form of computer-readable storage medium such that execution of the sequence of actions enables at least one processor to perform the functionality described herein. Furthermore, the sequence of actions described herein can be embodied in a combination of hardware and software. Thus, the various aspects of the present invention may be embodied in a number of different forms, all of which have been contemplated to be within the scope of the claimed subject matter. In addition, for each of the embodiments described herein, the corresponding form of any such embodiment may be described herein as, for example, "a computer configured to" perform the described action.

Figure 8:
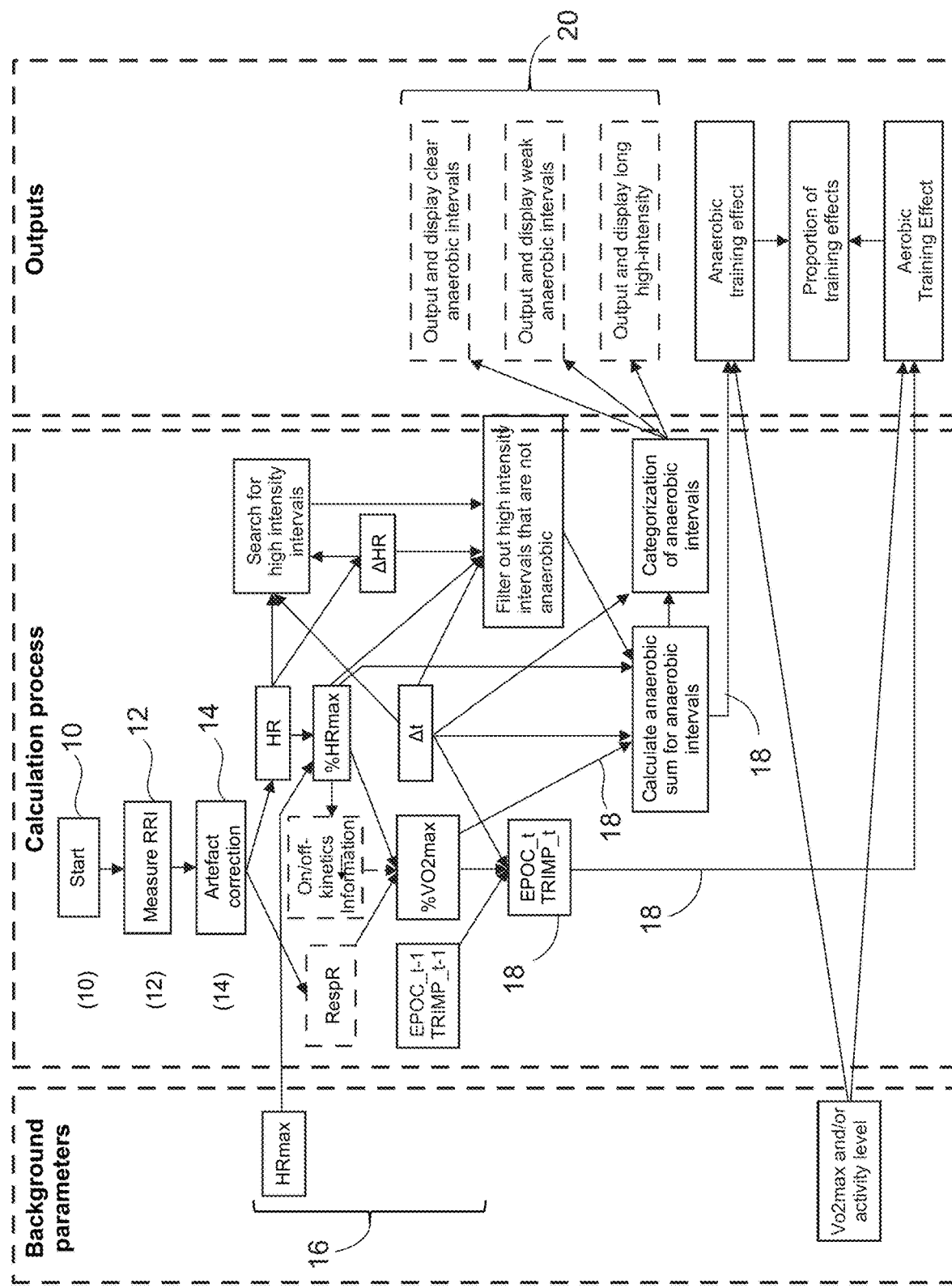
FIG. 8 represents an example of HR-only based calculation.
Figure 9:
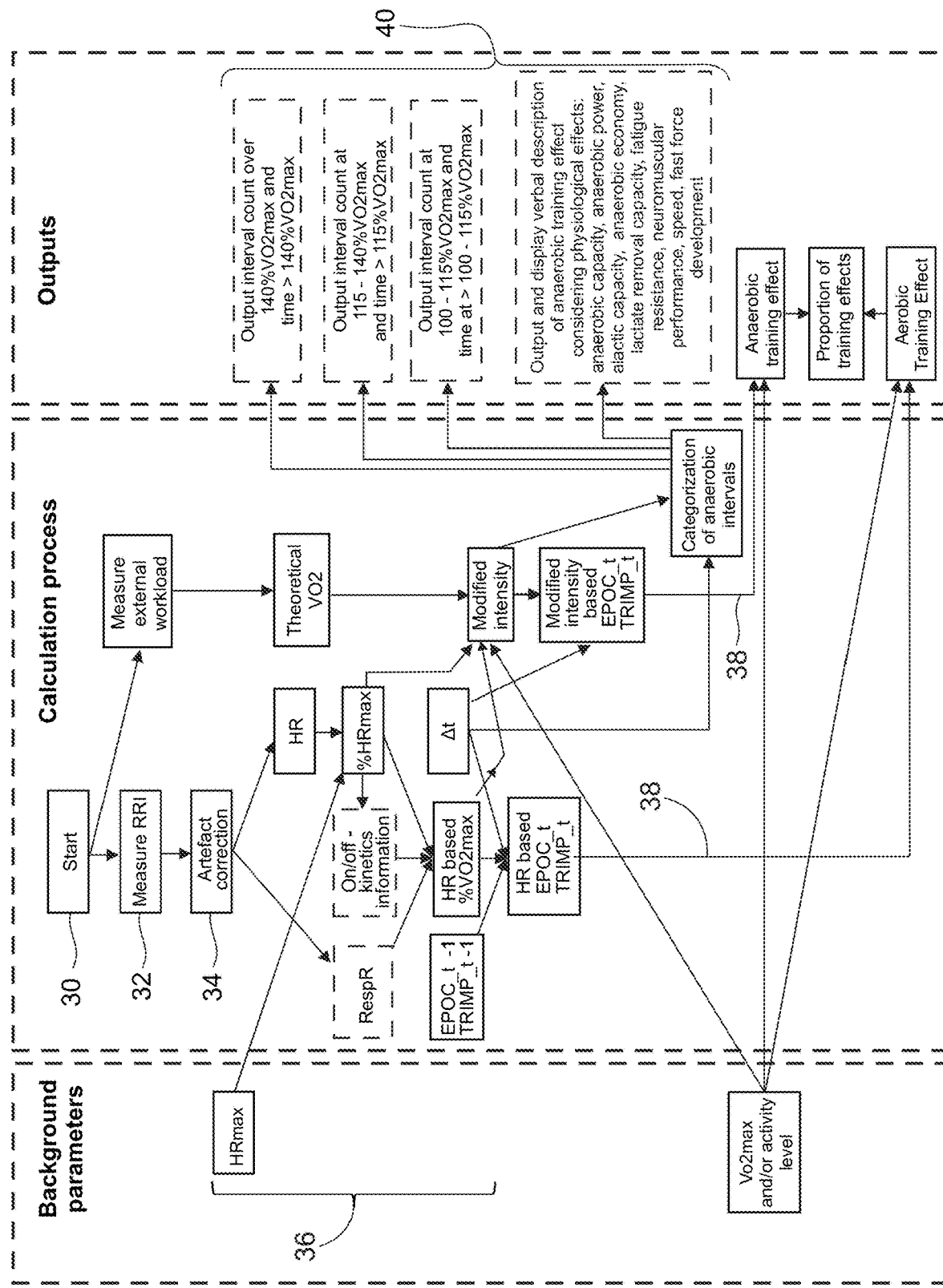
FIG. 9 represents an example of calculation in situation where both HR and external workload information are available.
Figure 10:
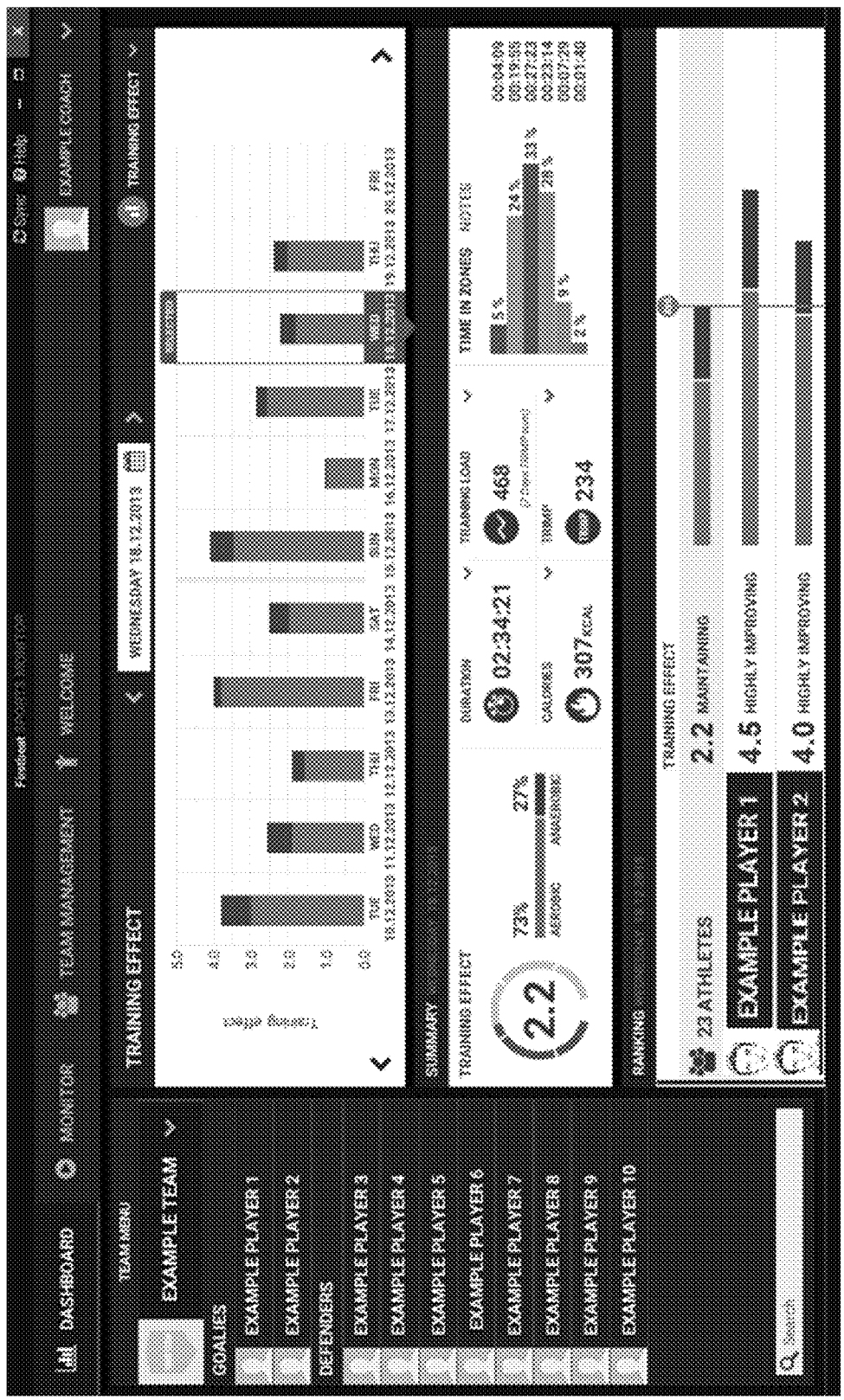
FIG. 10 represents an example of user interface with a display that allows comparison of different days as team level averages as well as player rankings within different days.

The method can be implemented in versatile devices, which have resources for measuring physiological responses (e.g. Oxygen consumption, heart rate, etc.) and external workload (e.g. speed and altitude or power output), and run software to execute processes depicted in the exemplary flowcharts of FIGS. 8 and 9. Model considering HR-only based calculation is disclosed in FIG. 8. The calculation has the following steps:

User starts measurement (10)
Beat to beat HR data (for example RR-intervals=RRI) or HR level data is collected (12)
Artifacts may be detected and corrected (14)
Searching high intensity intervals from corrected HR signal and filtering out high intensity intervals that are not anaerobic (16)
Calculating accumulated aerobic sum (e.g. EPOC/TRIMP) as well as anaerobic sum (e.g. EPOC/TRIMP)

and determining aerobic training effect and anaerobic training effect based on the sum values (18)

Interval-count and time in different high intensity training zones can be shown to a user (20)

Calculation comprising both HR and external workload is disclosed in FIG. 9. The calculation has the following steps:

User may start a measurement (30)

Beat to beat HR data (for example RR-intervals=RRI) or HR level data is collected. In addition, external workload is measured for example as speed & altitude or power output time series (32)

Artifacts may be detected and corrected (34) from HR data

Calculating modified intensity from corrected HR signal and external workload.

Calculating accumulated aerobic sum (e.g. EPOC/TRIMP) as well as anaerobic sum (e.g. EPOC/TRIMP) and determining aerobic training effect and anaerobic training effect based on the sum values (38)

Interval-count and time in different high intensity training zones can be shown to a user (40)

Figure 11:
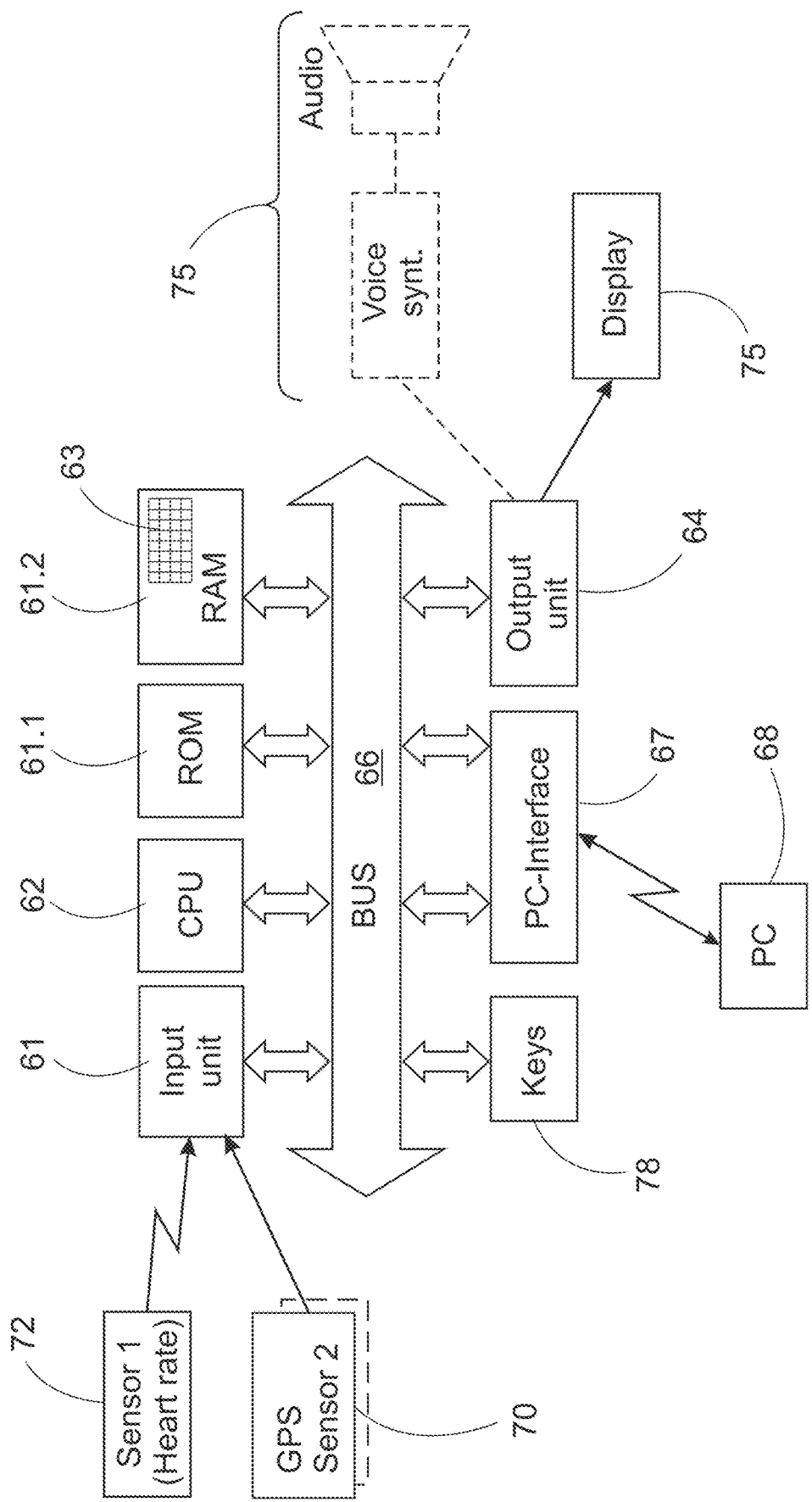
FIG. 11 represents an example of a hardware assembly.

A schematic hardware assembly is depicted in exemplary FIG. 11.

The system and method according to the exemplary embodiments can be applied in many kinds of devices as would be understood by a person of ordinary skill in the art. For example, a wrist top device with a heart-rate transmitter, a mobile device such as a phone, tablet or the like, or other system having CPU, memory and software therein may be used.

According to exemplary FIG. 11, in the implementation may include an assembly built around a central processing unit (CPU) 62. A bus 66 may transmit data between the central unit 62 and the other units. The input unit 61, ROM memory 61.1, RAM memory 61.2 including a buffer 63, keypad 78, PC connection 67, and output unit 64 may be connected to the bus.

The system may include a data logger which can be connected to cloud service, or other storage as would be understood by a person of ordinary skill in the art. The data logger may measure, for example, physiological response and/or external workload.

A heart rate sensor 72 and any sensor 70 registering external workload may be connected to the input unit 61, which may handle the sensor's data traffic to the bus 66. In some exemplary embodiments, the PC may be connected to a PC connection 67. The output device, for example a display 75 or the like, may be connected to output unit 64. In some embodiments, voice feedback may be created with the aid of, for example, a voice synthesizer and a loudspeaker 75, instead of, or in addition to the feedback on the display. The sensor 70 which may measure external workload may include any number of sensors, which may be used together to define the external work done by the user.

More specifically the apparatus presented in FIG. 11 may have the following parts for determining an anaerobic training effect:

a heart rate sensor 72 configured to measure the heart beat of the person, the heart rate signal being representative of the heart beat of the user;

optionally at least one sensor 70 to measure an external workload during an exercise, and a data processing unit 62 operably coupled to the said sensors 72, 70, a memory 61.1, 61.2 operably coupled to the data processing unit 62, the memory may be configured to save background information of a user, for example, background data including an earlier performance level, user characteristics, and the like.

The apparatus may include dedicated software configured to execute the embodiments described in the present disclosure.

In one exemplary embodiment initial background and personal data may be stored. For example, the performance level (for example VO2 max or METmax) and the maximum heart rate (HRmax), and the like, of the user may be stored. Personal data may be entered or determined beforehand.

In one exemplary embodiment, a person (e.g. an athlete or keep fit enthusiast) may start an exercise session. The type of exercise can be either interval or continuous, i.e. it can include breaks and rest periods. The user can freely decide the intensity of exercise, as well as recovery periods inside the exercise session. Heart beat data and performance data can be continuously measured (speed and altitude or power output) during the exercise using, for example, a heart rate monitor, wristop computer or other related device as would be understood by a person of ordinary skill in the art. Even a heart beat sensor that is connected to a mobile phone or PDA device (using for example Bluetooth connection) can be used, in which case the mobile phone or PDA device would measure external workload (speed and altitude) and serve as a CPU unit.

In further exemplary embodiments the user may exercise outdoors. Both heart rate (or other physiological signal) and external workload can be measured to achieve the most accurate analysis of anaerobic training effects. The user can exercise, for example, by walking, running, or playing sports such as football, rugby, field hockey, tennis, or any other sports. In some embodiments heart rate may be measured using a heart rate transmitter belt, or the like, and analyzed in a CPU-unit that can be, for example, a normal sports watch, wristop computer, or similar device as would be understood by a person of ordinary skill in the art. Alternatively, it may be possible to use ppg (photoplethysmograph)-signal processing so that both the measurement and analysis of data may be done using a wristop device, or the like. Measurement of speed and altitude can be done using a GPS signal. The GPS receiver may be embedded, for example, in the wristop device, but an external GPS receiver can be used as would be understood by a person of ordinary skill in the art. Altitude data can be retrieved from GPS data, additional barometer data, and the like. A barometer may be embedded in the wristop computer. In the described exemplary embodiments, a user may, for example, walk or run (or both) during the exercise. The terrain can be whatever the user wants, for example, hilly or flat. During the exercise, data points may be continuously filtered and/or validated. The Training Effect or any parameter calculated by the system can be shown to the user during the exercise, or after exercise, as desired.

In some of the above described exemplary embodiments, heartbeat data, speed data and altitude data may be gathered and used, for example, when the user is exercising on foot (walking/pole walking or running) outdoors. In still further exemplary embodiments, a WIFI technique, for example, may be used so that positioning can be performed indoors. It may also be possible to use an accelerometer signal (for example an accelerometer positioned on a user's foot or the like) to define walking/running speed indoors or outdoors, and that data can be used together with barometer data. It is also possible that the exercise is done using a treadmill, or the like. In that case, it is also possible that the speed data can be retrieved from an accelerometry signal, or the like. In one exemplary embodiment a user can input treadmill speed data to the CPU while the heartbeat data is continuously measured.

Furthermore, considering the embodiments that use both physiological and external workload data, it is also possible to determine the anaerobic training effect (or other such parameters) in other exercise modes: For example in cycling or rowing power output can be easily measured and retrieved. As would be understood by a person of ordinary skill in the art, power output can be measured in cycling, for example, using a power meter embedded in pedals or chains, and this power data can be shown to the user in a wristop device, or the like. In one exemplary embodiment related to cycling—speed and altitude data may be replaced with power output data measured from a bicycle. The user can do the bicycling exercise indoors or outdoors, and on any desired terrain.

Referring still generally to the exemplary embodiments, where physiological and external workload data are measured, (e.g. cycling or speed and altitude of walking or running are measured) it is possible to increase the accuracy of Training Effect estimate by measuring external workload data. This is because heartbeat data can be measured continuously as a function of performance data.

Since purely HR and/or HRV based assessment of anaerobic/aerobic training effect may be beneficial in some cases, these exemplary embodiments are presented below. Purely HR and/or HRV based assessment may be more desired for example in ice-hockey, skating or other sports where external work output is difficult to measure. In addition, positioning indoors is more difficult than outdoors that may lead athletes and coaches to select HR and/or HRV based assessment for indoor exercises.

In one exemplary embodiment disclosing a purely HR and/or HRV based assessment, the system constantly detects exercise intervals from periods of increasing and decreasing heart rate from the heart beat data. This is done by the system by calculating a moving average of 10 second heart rate difference. The average is calculated for each measurement point by weighting the differences (calculated for the surrounding points) by, for example, a 25 second Hanning window. The averaged heart rate differences are used to define the periods of increasing and decreasing heart rate that follow each other in the data. Of each detected period of increasing or decreasing heart rate, certain parameters are saved in the buffer memory. These are 1) the sum of the averaged heart rate differences during the period of increasing heart rates, 2) the sum of the averaged heart rate differences during the period of decreasing heart rates (the sums are hereinafter denoted by p for heart rate increases and n for decreases), 3) the initial heart rate of the heart rate increase, 4) the initial heart rate of the heart rate decrease (HRlow for a heart rate increase and HRpeak for a decrease), 5) the time point where HRlow or HRpeak was measured, as well as 6) the peak intensity as % VO2 max at the point of the HRpeak value. The aforementioned values are stored in timely order to a constant size data buffer. From the buffer, the oldest values are removed as new periods of increasing and decreasing heart rate are detected or as intervals are detected and/or accepted.

In another exemplary embodiment, the information stored in the data buffer is used to detect exercise intervals when some of the following apply: 1) a maximum amount of increasing and decreasing heart rate periods has been stored in the buffer, or 2) the heart rate level has decreased at least 10 bpm (beats per minute) and the duration of the heart rate decrease has been at least 30 seconds, or 3) the heart rate level drops below 70% of the personal maximum HR. The heart rate data stored in the buffer is used to detect intervals by calculating a value/that represents the interval-likeness of a measured heart rate time sequence. These sequences start from a heart rate increase (buffer index i) and end to a heart rate decrease (index f). Such sequences are defined for all values of i and f (i≤f) that are stored in the buffer. The interval-likeness is calculated for each of these sequences. The affecting factors include heart rate derivatives, heart rate differences, and the duration of the sequence. The following formula can be used:

$$I=(HR_{peak,f}-HR_{low,i})+p_i+n_f+\min(p_i,n_f)-l/50-Y, \quad (4)$$

where $HR_{peak,f}$ is the last local heart rate peak value inside the sequence, and $HR_{low,i}$ is the initial heart rate of the sequence. The duration of the interval l is the duration between $HR_{low,i}$ and $HR_{peak,f}$ in seconds. The sum $p_i$ corresponds to the first heart rate increase in the sequence and $n_f$ corresponds to the last heart rate decrease, and $\min(p_i, n_f)$ is the smaller of these two. The term Y describes the effect of the heart rate changes within the sequence and is calculated as $$Y=\sqrt{\Sigma_{j=i+1}^{f}p_j^2+\Sigma_{k=i}^{f-1}n_k^2}. \quad (5)$$

In one exemplary embodiment, intervals are accepted for later analysis. For the sequence to be accepted as an interval, certain rules must be fulfilled. These may be 1) the value I must be higher than a threshold value, and it must be greater than those of other time sequences that include some of the same heart rate increases and decreases than the sequence of interest (i.e. the time sequences are partly or totally overlapping), 2) the recovery time from the preceding interval must be longer than 30 seconds or $HR_{low,i}$ must be lower than 70% of the personal maximal heart rate, 3) the highest heart rate of the sequence must be higher than 80% of the personal maximal heart rate, 4) the duration of the sequence must be longer than 15 seconds, 5) the peak value for % VO2 max must be higher than 73%, and 6) the difference $HR_{peak,f}-HR_{low,i}$ must be sufficiently high (the required difference is the larger the lower the value of $HR_{low,i}$ is). If the sequence is accepted as an interval, the heart rate information of the sequence and of those preceding it is removed from the data buffer.

In other exemplary embodiment, detected intervals can be used to calculate accumulated anaerobic sum of exercise. The total anaerobic sum of exercise may be the sum of 1) the anaerobic sum calculated for intervals and 2) the anaerobic sum of long continuous high intensity exercising. One significant determinant of anaerobic sum may be the duration of the interval. Duration is further multiplied by four factors which describe the properties of the interval (see FIG. 4). These factors are 1) duration of the interval, 2) peak intensity of the interval as % VO2 max, 3) the starting heart rate level of the interval that describes the recovery level, and 4) the difference between the moving HR average at the start of the interval and the HRpeak value inside the interval. The duration affects in principle so that the shorter the duration the higher the multiplier. If the duration of the interval is longer than a maximal threshold value, for example 300 seconds, the effective duration value used in the anaerobic sum calculation can be fixed to the threshold value, so that the anaerobic sum of longer intervals will not be zero. The second multiplier is the higher the higher the peak intensity (% VO2 max) of the interval (note that the interval is rejected if the peak intensity is not high enough). The third multiplier is the higher the lower the heart rate is when the interval starts, i.e. the better the recovery level at the onset of the interval. The fourth multiplier is directly proportional to the difference between the HRpeak value and a moving average calculated from the HR values before the start of the interval.

In another exemplary embodiment, in addition to the aforementioned multipliers, also the fluctuations in heart rate within the interval describing noticeable changes in working intensity can be taken into account. The fluctuation can affect the calculated anaerobic sum when the intensity is high enough, for example at least 80% of the personal maximum heart rate. More anaerobic sum can be calculated when there are significant and regular fluctuations in heart rate within an interval. This fluctuation based anaerobic sum can be calculated by the formula $$\Sigma_i a \cdot \min(n_i, p_i), \quad (6)$$

where $n_i$ and $p_i$ correspond to the decrease in heart rate before the local minimum heart rate (indexi) and the increase in heart rate after the local minimum heart rate, respectively. The sum is calculated over the local minimums within the interval.

The factor α can be affected by the factors described in the previous exemplary embodiment.

In another exemplary embodiment, anaerobic sum may be calculated cumulatively from the measured HR data at each point of the exercise even in the case of steady state exercise (=non-interval periods). The amount of the cumulative anaerobic sum can be affected for example by the temporal value of HR signal, time derivative of HR signal, local lowest and peak values of HR signal, average of the HR signal, and personal background parameters (for example anaerobic threshold heart rate, VO2 max etc.). For example, when the intensity is above 90% HRmax, the rate of increase of the cumulative anaerobic sum may be directly proportional to the intensity, so that at 100% HRmax intensity the cumulative anaerobic sum can increase for example 0.06 units/s. This is in line with physiology since there is always anaerobic metabolism, especially above the anaerobic threshold heart rates or intensities.

Figure 5:
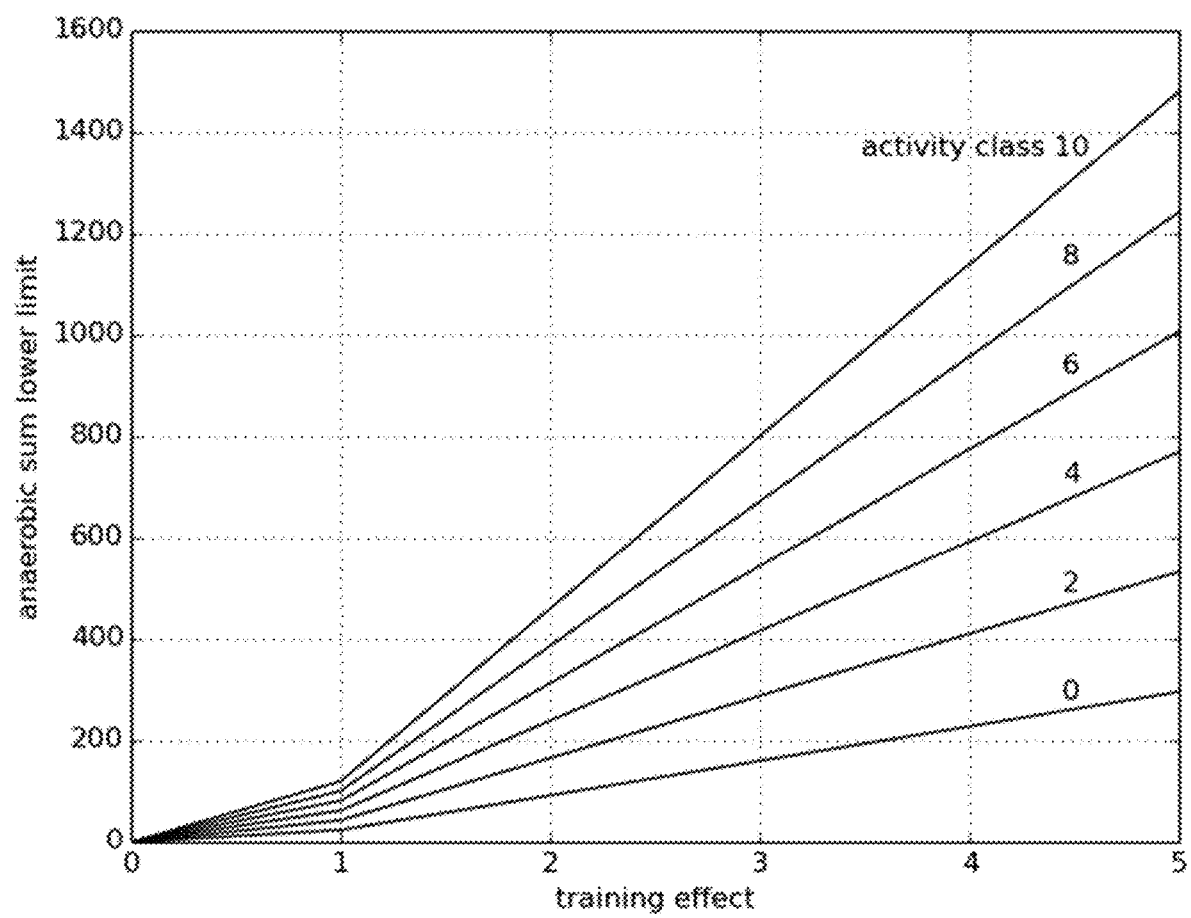
FIG. 5 represents an example of scaling of anaerobic sum into a training effect value wherein activity class has an effect on the scaling. For the person with higher physical fitness, higher anaerobic sum is needed to achieve similar training effect than for a person with poorer physical fitness level or lower activity level.
Figure 6:
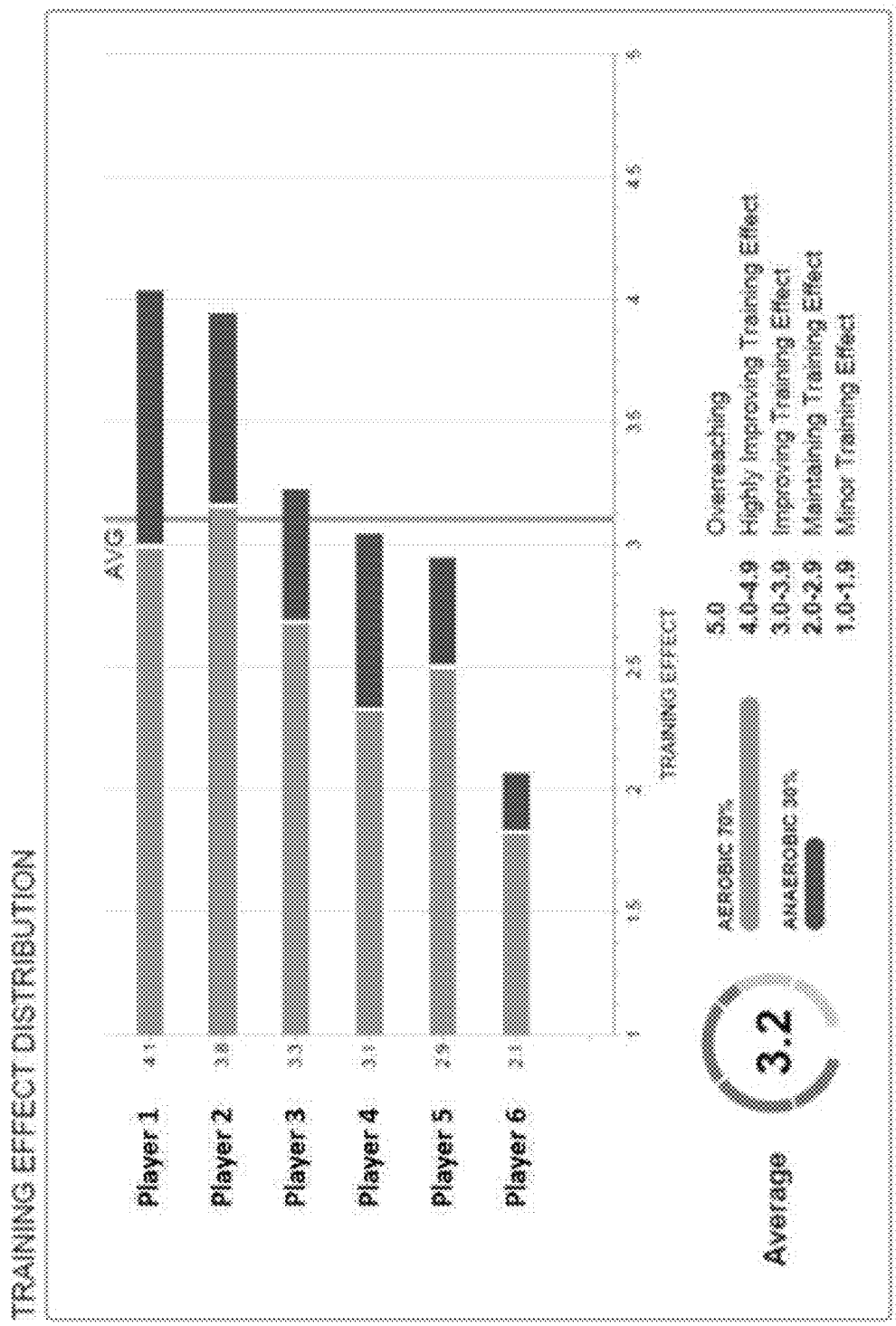
FIG. 6 represents an example of user interface with a summary view wherein the contribution of aerobic and anaerobic training effects, and the total training effect of several athletes is shown on a single display.

In other exemplary embodiments, anaerobic sum can be used in determining the anaerobic training effect with linear functions. The properties (derivative and zero) of the functions are affected by the user's activity level or fitness level. Examples of such functions can be found in FIG. 5. For the person with higher physical fitness, higher anaerobic sum is needed to achieve similar training effect than for a person with poorer physical fitness level or lower activity level.

In one exemplary embodiment, each user's individual anaerobic threshold may be inputted to the system. This may be performed manually, from software or by recognized automatically from exercise parameters (heart rate beat interval data and external workload data required). Individual anaerobic threshold can be used to modify the calculations in order to recognize and take into account more individually the anaerobic work performed. For example, the effect of exercise intensity during intervals can increase the calculated anaerobic sum if the user's anaerobic threshold is lower than default value 90%. In similar fashion, if a person's anaerobic threshold is higher than default 90%, e.g. 93%, less anaerobic sum may be calculated.

In one exemplary embodiment, the time between the detected and/or accepted intervals calculated by the system can be defined to represent recovery time between the intervals.

In one exemplary embodiment, after the intervals have been detected, information regarding the intervals can be provided for the user in real-time or any time after the exercise. These information may include for example number of intervals, intervals distribution to different categories (such as clear anaerobic, weak anaerobic, long interval), the intensity (e.g. average, peak, and lower level of intensity) during intervals, duration of intervals, duration of recovery phases, parameters defining recovery phases (e.g. average, peak, and lower level of intensity), the overall anaerobic sum calculated, the anaerobic sum calculated within intervals, the anaerobic sum calculated outside intervals (i.e. by continuous high-intensity exercising). The information and feedback, of the examples above, can be provided to the user in visual, numerical and verbal form, and this may include all or some of the aforementioned parameters but not limited to these.

In one exemplary embodiment, information on aerobic and anaerobic training effect may be provided to the user. The training effect can include the overall training effect (the highest of aerobic and anaerobic training effect), both or one of the training effects (aerobic and anaerobic), and the distribution of training effect into aerobic and anaerobic.

A practical example of anaerobic sum calculation based on anaerobic interval detection Anaerobic interval detection During one time period of a high intensity interval training, heart rate (HR) behaves as follows.

From 90 bpm to 170 bpm in 1 minute; from 170 bpm to 140 bpm in 30 seconds; from 140 bpm to 165 bpm in 30 seconds; from 165 bpm to 100 bpm in 1 minute.

Hereby the duration l of the period is 180 seconds, and the values of the positive and negative changes in HR, $p_i$ and $n_i$, are $p_1=80, n_1=30, p_2=25, n_2=65$.

The interval likeness of the period can now be calculated according to the equations (4) and (5) as $$I = (165-90)+80+65+\min(80,65)-180/50-\sqrt{25^2+30^2} \approx 242$$

The period is now determined to have the following properties.

The interval likeness of the period is higher than an empirically determined threshold value.

The interval likeness of the period is higher than any other periods comprising of some of the HR changes inside the period.

The recovery time preceding the period (time between the previous potential anaerobic interval and the period) is longer than 30 seconds.

The maximum HR value is above 80% HRmax.

The length of the period is between 15 and 200 seconds.

The difference between the maximum HR value and the initial HR value is higher than 20 bpm.

Based on these properties, the period is now validated as a proper anaerobic interval.

Calculation of the anaerobic sum

The anaerobic sum (the "anaerobic effect") of the interval is now calculated by multiplying the duration of the interval, 180 seconds, by the coefficients shown in FIGS. 4a-4d. The affecting coefficients are related to Interval duration(coefficient value=0.25)

Peak % VO2 max(coefficient value=1.1)

The difference between peak % HRmax and initial % HRmax moving average, and (coefficient value=1.0)

Initial % HRmax(coefficient value=1.0)

After applying the coefficients to the duration of the interval, the resulting anaerobic sum is 49.5.

Additional anaerobic sum based on the HR fluctuations is calculated by the equation (6) to be 2.5·min(30,25)=62.5

Hereby the total anaerobic sum of the anaerobic interval is 49.5+62.5=112.

The minimum buffered information needed here comprises rise and fall information; % HRmax-differences, timestamps, peak values of % VO2 max (or % HRmax).

In following exemplary embodiments, information on performed external work (e.g. pedaling power in cycling OR speed/altitude changes in running) can be used to compare theoretical oxygen consumption to heart beat based oxygen consumption to assess energy provided by anaerobic energy pathways, and to assess training effect achieved using both of the energy pathways. This information can support or substitute the HR/HRV based calculation of anaerobic sum. Of course, use of purely heart rate-based estimation of anaerobic and aerobic training effect enables application of the method in all sports. Use of speed and altitude (e.g. running) or power output (cycling, rowing or other exercise equipment) allows even a more detailed analysis of anaerobic training effect. In addition, measurement of power during running has recently become possible. Running power can be measured using either speed and altitude OR speed/altitude in combination with acceleration.

One exemplary embodiment comprising speed/altitude or power measurement comprises the following steps:
1. Heart rate and external work output (speed+altitude or power output) are measured during a user performed exercise session
2. Modified intensity (=theoretical VO2) can be calculated using weighted average of heart rate and external workload. External workload can be determined using either the combination of speed and altitude, or power output alone. The resulting value (e.g. ml/kg/min) may be divided by person's maximal oxygen uptake to get proportional intensity (% VO2 max) estimate.
    a. It is also possible to calculate modified intensity solely based on external workload. However, combining information on external workload with heart rate in formation may significantly stabilize modified intensity value.
3. Proportional intensity (% VO2 max) estimate is calculated based on heart beat data.
4. EPOC value is pre-predicted during the exercise using the % VO2 max estimate derived from modified intensity
5. EPOC value is pre-predicted during the exercise using the % VO2 max estimate derived from heart beat data
6. Calculating continuously two different Training Effect (TE) estimates based on two different EPOC values
7. Selecting the higher Training Effect value to represent the total Training effect of the exercise or presenting both TE values simultaneously to the user
8. If willing to provide aerobic and anaerobic TE contribution to a user, dividing HR based EPOC estimate by the EPOC estimate derived from work output. Alternatively, HR based TE can be divided by Total TE.

Figure 2:
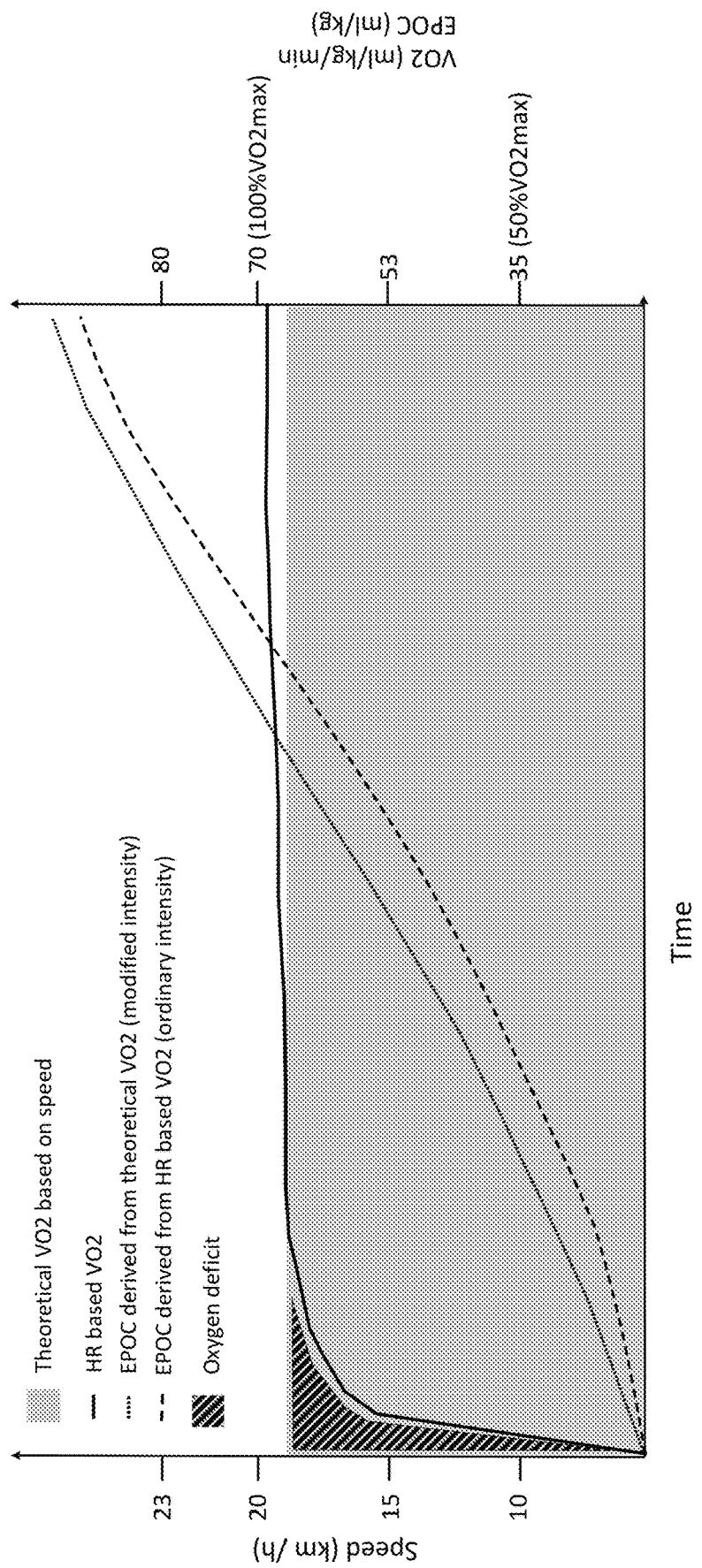
FIG. 2 represents a hard steady pace exercise where external workload based EPOC (=modified intensity based EPOC; modified intensity can be calculated also solely based on heart rate information) accumulates only slightly above HR based EPOC. Exercise has no anaerobic training effect.

As can be seen from the FIG. 1, theoretical VO2 based EPOC values get higher values than HR based EPOC values during an interval exercise. The figure presents and interval workout having intervals of 3×15 km/h+3×20 km/h+3×23 km/h wherein each interval is followed by an active recovery period including running with 10 km/h speed. Duration of recovery running periods is equal to high intensity running periods. The runner in this example has VO2 max of 70 ml/kg/min that corresponds to running speed of 20 km/h on running track. As can be seen from the figure, when running 20 km/h or slower accumulation of HR based EPOC is only slightly slower when compared with EPOC derived based on Theoretical VO2. This is because HR based VO2 estimate (that reflects the actual VO2 of the runner) reaches theoretical VO2 (that describes the actual need for oxygen for any given speed) during the intervals that are run below VO2 max intensity (=20 km/h=70 ml/kg/min). With higher intensities theoretical VO2 is significantly higher than HR based VO2, which causes the increasing gap between the two EPOC estimates. From a physiological point of view the EPOC value derived based on theoretical VO2 is much more accurate in describing total EPOC since it well reflects the increasing gap between body's oxygen requirement and oxygen supply. The difference in body's oxygen requirement and oxygen supply results in increasing oxygen deficit that is "paid" after exercise as oxygen debt. Actually, EPOC is only partly caused by oxygen debt as there are many other components affecting: for example, exercise induced elevated body temperature, respiratory activity, increased level of catecholamine's etc. Calculation method for EPOC is the same but the difference is largely due to the fact that Theoretical VO2 in this example reaches values up to 114% VO2 max whereas HR-based VO2 can only reach values up to 100%. The two calculated EPOC peak values are 74 ml/kg and 94 ml/kg for HR based and theoretical VO2 based EPOC, respectively. Accordingly, the runner may be shown that total training effect was 3.5 and the effect was 79% aerobic (=74/94) and 21% (=20/94) anaerobic. An opposite example is presented in FIG. 2 where same person has performed a hard submaximal steady pace exercise where heart rate based EPOC is 91 ml/kg and theoretical VO2 based EPOC 94 ml/kg. Accordingly, total training effect is 3.5 but aerobic contribution is 97% and anaerobic contribution is only 3%.

Although prior art discloses comparison of used energy systems during exercise it does not provide means to estimate the actual training effect. Actually, comparison of proportions of aerobic and anaerobic energy yield is usually not meaningful since in long exercises most of energy is produced aerobically even if exercise would include hard anaerobic periods. On the contrary, EPOC provides a more sophisticated measure for training effect as it is a well-established measure of training effect. EPOC actually reflects the extent of disturbance in body's homeostasis caused by exercise. EPOC can be modelled, for example, using neural network modelling with a large amount of experimental data.

In such a case, total training effect is calculated using HR based EPOC (that is higher) and the aerobic effect would be 100% and anaerobic effect 0%. This makes sense also from a physiological point of view since actual measured VO2 has a slow component meaning that in prolonged exercises VO2 drifts to a higher level than theoretical VO2.

For example, the following calculation formulas can be used for theoretical VO2:

Theoretical VO2 of running (ml/kg/min)=0.2*(speed m/min)+0.9*(speed m/min)*TAN(grade of incline)+3.5      (5)

Theoretical VO2 of walking (ml/kg/min)=1.78*(speed m/s)*60*(TAN(grade of incline)+0.073)

A threshold speed of e.g. 7.5 km/h can be used in switching from walking formula to running formula. Alternatively, detection between walking and running can be used using accelerometer data.

In cycling, power output can be converted to VO2 using the following exemplary formula:

Theoretical VO2 of cycling (ml/kg/min)=((power watts)*12+300))/person's weight

Theoretical VO2 (Indoor) rowing VO2 (ml/kg/min)= (14.72*Power+250.39)/person's weight In addition, equations have been described for the calculation of road cycling power based on measured speed and altitude data etc. based on which % VO2 max can be calculated.

In one exemplary embodiment the accuracy of theoretical VO2 calculation is improved in interval type sports. As is known in the art, theoretical VO2 of accelerated or decelerated running at any given speed differ significantly from steady-speed running. For example, during acceleration phase a runner may have an average speed of 15 km/h during a sampling period. In this case, for example, if initial speed has been 0 km/h and end speed 30 km/h, the average value of 15 km/h provides too low estimate of theoretical VO2. Accordingly, using acceleration as a multiplying factor the error can be avoided.

In one exemplary embodiment HR-only based calculation of anaerobic training effect can also be applied without interval detection. In that case calculation would go as follows:
  a) A user starts to exercise;
  b) Heart rate (beat-by-beat heart rate or HR-level) of a user is continuously measured and recorded with time stamp,
  c) Unreliable data points, such as ectopic beats of heart rate may be filtered or corrected by signal processing first, and remaining points may form accepted data points;
  d) Determining user's modified intensity (% VO2 max) from data utilizing information on e.g. HR level relative to his/her maximal heart rate (% HRmax), RRI derived respiration (if R-R intervals are available) and heart rate derivative (e.g. % HRmax) and VO2 derivative (e.g. % VO2 max)
     The calculated modified intensity gets higher when 1) HR level goes closer to HRmax, 2) respiration rate increases 3) when HR increases rapidly
  e) Calculating aerobic EPOC using ordinary HR derived intensity
  f) Calculating anaerobic EPOC using modified intensity
     Modified intensities lower than a predetermined limit (e.g. 80% VO2 max) may be excluded from calculation if only the anaerobic contribution of high intensity work periods is regarded meaningful. (there is always overlap in energy production meaning that even low intensity exercise has little anaerobic contribution. Anaerobic contribution of energy production increases significantly above anaerobic threshold intensities that is commonly around 80% VO2 max)
  g) Determining total anaerobic Training Effect by scaling aerobic and anaerobic EPOC values and optionally their derivatives. Training effect classification may be based on commonly known coaching science, i.e. anaerobic work quantities in different exercises. In addition, physical fitness level of a person may be taken into account when evaluating the anaerobic load of the performed exercise. In principle, a person with higher fitness level (or activity level) needs to get higher EPOC to achieve similar training effect;
     In similar fashion, the performed aerobic EPOC is calculated and scaled during exercise by comparing measured aerobic EPOC to reference values for aerobic work. Person's physical fitness level may be taken into account when classifying the calculated EPOC. Classification may comprise aerobic training effect having values typically between 1 and 5, and having a verbal description between minor and overreaching training effect.
  h) Providing aerobic and anaerobic training effect values or their proportions to the user
  i) Although there is no actual interval detection method, it is also possible to calculate time periods that exceed predetermined limit values. For example, periods having modified intensity higher than 100% can be regarded as moderate anaerobic intervals. Periods having modified intensity higher than 115% can be regarded as high intensity anaerobic intervals. Periods having modified intensity higher than 140% can be regarded as high speed anaerobic intervals. These intensity limits can be fixed but preferably they change linearly based on user's fitness level.
  j) When total anaerobic TE and the number of exercise periods (=intervals bouts) above predetermined intensity values are known (at any moment of exercise) it is possible to give feedback sentences (See table 1 in FIG. 15 and table 2 in FIG. 16) regarding achieved exercise benefits.
  k) Also other characteristics of different exercise periods can be presented to the user, for example average duration and intensity of intervals.

Implementation of calculation without having interval detection as a mandatory step may not have as high requirements for calculation power/memory. Therefore it may be more suitable to be used in commercial wristop computers or heart rate monitors. In addition it may allow better correspondence of results in an end user devices when similar exercises have been done with and without information on external work output—for example on one day user may perform interval workout outside having GPS enabled whereas on another day he/she might perform the workout inside on a treadmill. Of course, user expects that results are similar even if the input parameters used in calculation might be different. In this exemplary embodiment modified intensity based model may be implemented in a way that it combines information on HR and external work output (GPS) to provide final estimate of intensity (modified intensity). Of course, HR based model works solely using HR information. Having HR information included in both models stabilizes results: For example, results from treadmill workout (without speed information) correspond well with outside running results (with speed information). This approach may also stabilize results because both HR and external work output signals may always include error peaks even if various artifact correction algorithms are applied. Averaging may correct error peaks on one part. In addition, model may be implemented in a way that boosting effect for external work output estimate (=modified intensity; can be calculated either solely based on heart rate or solely based on theoretical VO2 or by combining HR information with theoretical VO2 information) is applied only when both measures show similar trends: E.g. detected high speed peaks in GPS signal may be excluded if HR trend does not show the same phenomenon or vice versa.

In one exemplary embodiment combination of aerobic and anaerobic training effects is utilized in determining recovery time from exercise. Tables 3 and 4 show examples of how recovery time can be linked to different TE values. In one exemplary embodiment higher one of recovery values is exposed to the user.

TABLE 3

Example of recovery time accumulation with respect to different aerobic training effect values

| Training effect | Recovery time in hours |
|---|---|
| 1.0: | 0.1 |
| 1.1: | 1.0 |
| 1.2: | 2.0 |
| 1.3: | 3.0 |
| 1.4: | 3.9 |
| 1.5: | 4.9 |
| 1.6: | 5.9 |
| 1.7: | 6.8 |
| 1.8: | 7.8 |
| 1.9: | 8.8 |
| 2.0: | 9.7 |
| 2.1: | 10.7 |
| 2.2: | 11.7 |
| 2.3: | 12.6 |
| 2.4: | 13.6 |
| 2.5: | 14.6 |
| 2.6: | 15.5 |
| 2.7: | 16.5 |
| 2.8: | 17.5 |
| 2.9: | 18.4 |
| 3.0: | 19.4 |
| 3.1: | 20.4 |
| 3.2: | 21.3 |
| 3.3: | 22.3 |
| 3.4: | 23.3 |
| 3.5: | 24.2 |
| 3.6: | 26.4 |

TABLE 3-continued

Example of recovery time accumulation with respect to different aerobic training effect values

| Training effect | Recovery time in hours |
|---|---|
| 3.7: | 28.8 |
| 3.8: | 31.2 |
| 3.9: | 33.6 |
| 4.0: | 36.0 |
| 4.1: | 38.4 |
| 4.2: | 40.8 |
| 4.3: | 43.2 |
| 4.4: | 45.6 |
| 4.5: | 48.0 |
| 4.6: | 52.8 |
| 4.7: | 57.6 |
| 4.8: | 62.4 |
| 4.9: | 67.2 |
| 5.0: | 72.0 |

TABLE 4

Example of recovery time accumulation matrix with respect to different anaerobic training effect values and detected intensities.

| | Anaerobic TE | | | | | |
|---|---|---|---|---|---|---|
| | 1.0-1.4 | 1.5-1.9 | 2.0-2.9 | 3.0-3.9 | 4.0-4.9 | 5.0 |
| No other conditions | Rec time 0-11 h | Rec time 12-23 h | Rec time 24-47 h | Rec time 48-71 h | Rec time 72-95 h | Rec time 96 h |
| High speed or power detected in several repeats | Rec time 0-17 h | Rec time 17-35 h | Rec time 36-59 h | Rec time 60-81 h | Rec time 82-95 h | Rec time 96 h |
| Moderate anaerobic exertion detected in several repeats | Rec time 0-11 h | Rec time 12-23 h | Rec time 24-47 h | Rec time 48-71 h | Rec time 72-95 h | Rec time 96 h |
| Easy anaerobic exertion detected in several repeats | Rec time 0-11 h | Rec time 12-23 h | Rec time 24-47 h | Rec time 48-71 h | Rec time 72-95 h | Rec time 96 h |

In one exemplary embodiment anaerobic recovery time is calculated as a function of anaerobic TE value (see table 5). In addition to that high speed periods may be weighted in a way that they may boost recovery time upwards with additional recovery time Additional recovery time may accumulate as follows:

Additional recovery time in minutes=10*time over 140% VO2 max(sec)+3.33*time over 115% VO2 max (sec)

In one exemplary embodiment maximum additional recovery time is 24 h. Accordingly, an exercise with 3.0 aerobic training effect, 3.0 anaerobic training effect and 150 second of exercise above 140% VO2 max would produce 25.8 h+24 h=49.8 h of recovery time.

TABLE 5

Example of recovery time accumulation with respect to different anaerobic training effect values.

| Anaerobic Training Effect | Anaerobic recovery time in hours |
|---|---|
| 0-0.9 | 0 |
| 1 | 0.1 |
| 1.1 | 1.4 |
| 1.2 | 2.7 |
| 1.3 | 3.9 |
| 1.4 | 5.2 |
| 1.5 | 6.5 |

TABLE 5-continued

Example of recovery time accumulation with respect to different anaerobic training effect values.

| Anaerobic Training Effect | Anaerobic recovery time in hours |
|---|---|
| 1.6 | 7.8 |
| 1.7 | 9.1 |
| 1.8 | 10.4 |
| 1.9 | 11.7 |
| 2 | 12.9 |
| 2.1 | 14.2 |
| 2.2 | 15.5 |
| 2.3 | 16.8 |
| 2.4 | 18.1 |
| 2.5 | 19.4 |
| 2.6 | 20.7 |
| 2.7 | 21.9 |
| 2.8 | 23.2 |
| 2.9 | 24.5 |
| 3 | 25.8 |
| 3.1 | 27.1 |
| 3.2 | 28.4 |
| 3.3 | 29.7 |
| 3.4 | 30.9 |
| 3.5 | 32.2 |
| 3.6 | 35.1 |
| 3.7 | 38.3 |
| 3.8 | 41.5 |
| 3.9 | 44.7 |
| 4 | 47.9 |
| 4.1 | 51.1 |
| 4.2 | 54.3 |
| 4.3 | 57.5 |
| 4.4 | 60.6 |
| 4.5 | 63.8 |
| 4.6 | 70.2 |
| 4.7 | 76.6 |
| 4.8 | 83.0 |
| 4.9 | 89.4 |
| 5 | 95.8 |

In one exemplary embodiment the described invention is applied during automatically guided workouts where user exercises with a wristop computer, mobile phone or other similar device. In such a case user may select a target training effect for the workout or the target is selected automatically from e.g. a training plan. During the workout guidance is given to the user by utilizing either auditory (voice guidance), visual (guidance using text, pictures or symbols) or kinesthetic (vibration) feedback. The content of feedback helps the user in reaching the target in a comfortable way. In addition to target training effect, also training duration and/or distance can be preset. Exercise bank can be utilized in the way that several different exercise types are optional to the user: for example steady pace exercises, long intervals, and short intervals.

Figure 3:
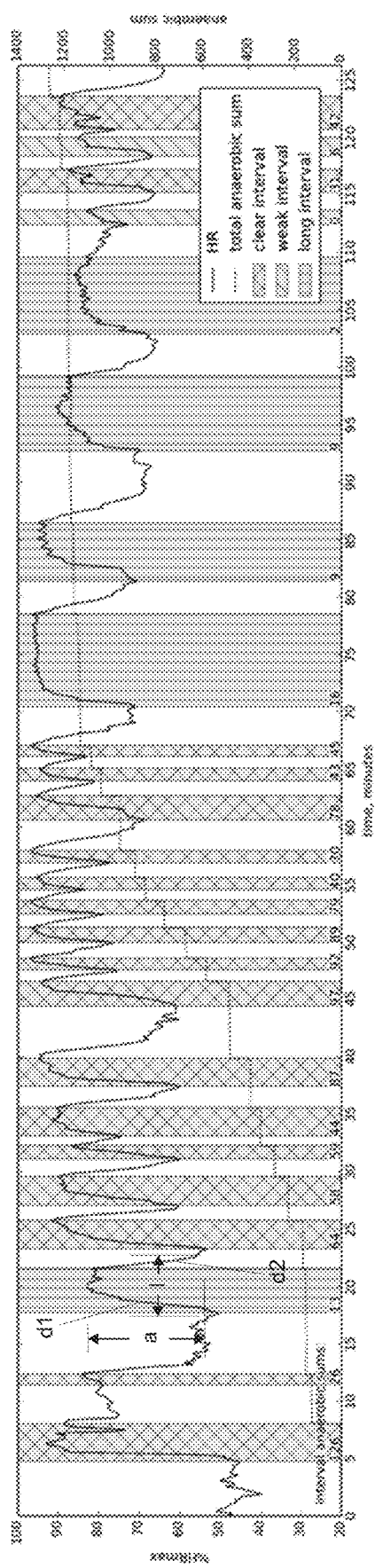
FIG. 3 represents an example of interval detection wherein exercise consists of a plurality of different intervals. In connection with detection intervals can be classified into different classes based on their characteristics (intensity gradient, peak or average intensity and duration).
Figure 4D:
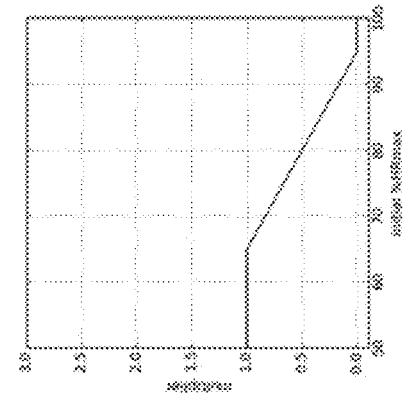
FIGS. 4*a*-4*d* represent an example of possible effects of different interval characteristics on accumulation of anaerobic sum: Interval duration, interval peak intensity (% VO2 max), HR difference between initial level and highest intensity during the interval, and initial HR level (% HRmax).
Figure 4C:
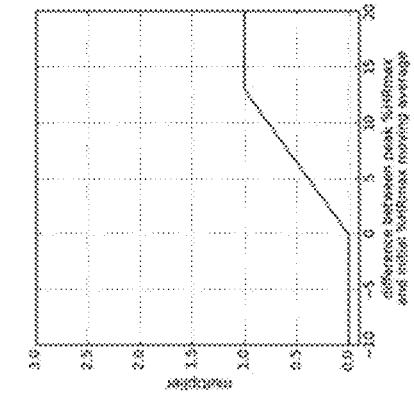
Figure 4B:
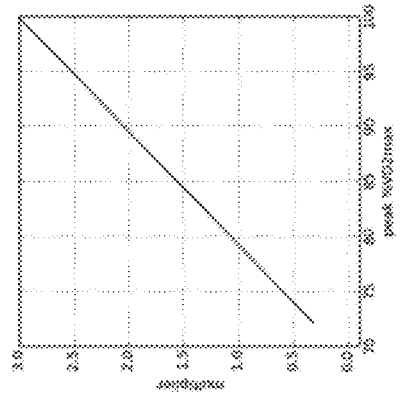
Figure 4A:
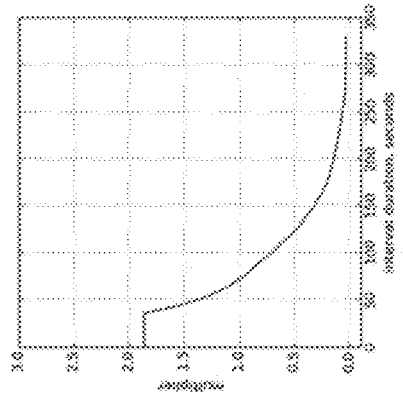

FIG. 3 presents an exercise having a plurality of intensity intervals. Usually a starting edge d1 (rising derivative), amount a, falling edge d2 (falling derivative) and duration 1 of a intensity interval are clearly visible in a HR/time-chart. These are characteristics of that intensity interval. A straightforward manner to determine the anaerobic training effect achieved during the exercise is to determine each interval with its starting and ending points and its intensity as well as duration by using memory buffer during recorded exercise. After detection of these parameters anaerobic training effect can be determined by utilizing information on interval duration as well as different weighting methods described in FIG. 4. However, that kind of calculation would need still a lot of hardware resources.

Figure 12:
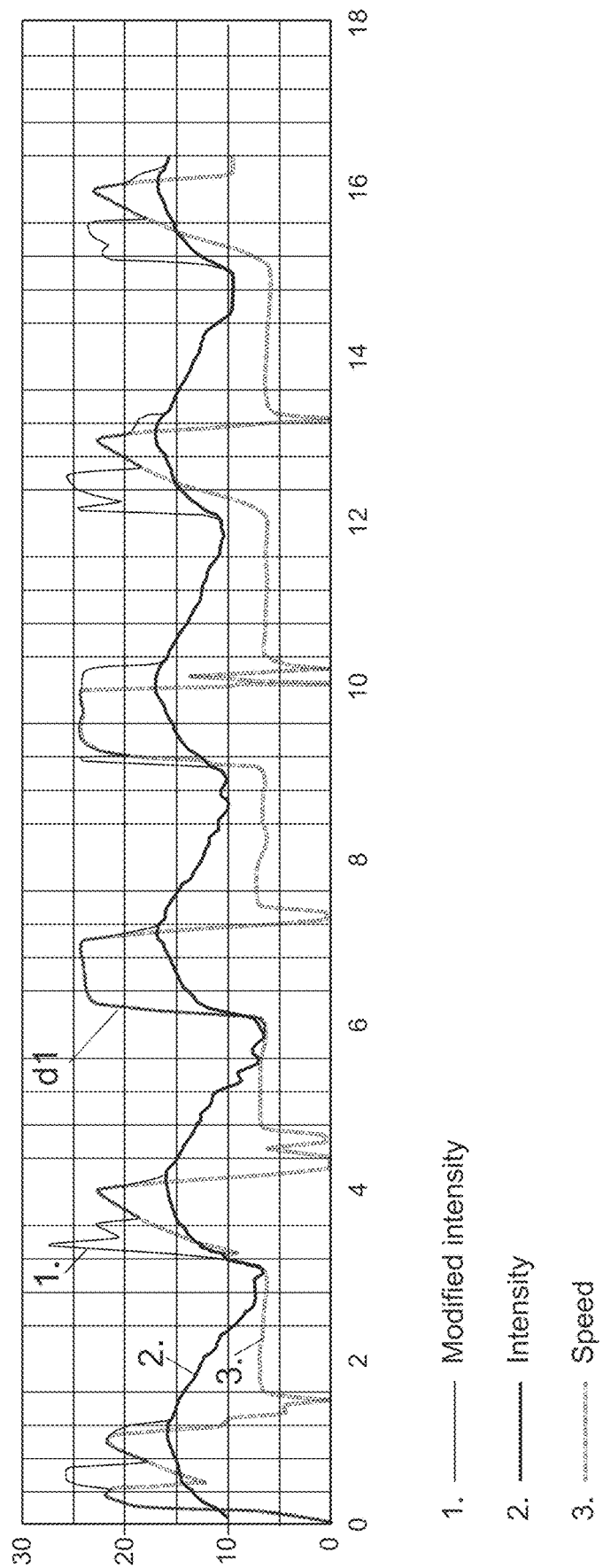
FIG. 12 represents an example of embodiment where speed, altitude and HR information are utilized in determining modified intensity. As can be seen, modified intensity can reach much higher values than one what might expect based on HR-level information. As is known from literature MET values correspond to km/h values very well in running. As can be seen from the figure modified intensity matches well with measured speed. Surprisingly, modified intensity corresponds well with speed (km/h) even when it is calculated solely based on heart rate.

FIG. 12 presents results of an intelligent calculation for anaerobic intensity in an exercise using minimum amount of memory. An ordinary training effect TE is calculated as taught in U.S. Pat. No. 7,192,401 B2 which is incorporated herein. Intensity is monitored by a heart rate sensor and preferably by another sensor sensing output power, like speed. The ordinary training effect TE (may be in terms of EPOC) is determined in a known manner. This disclosure presents now a method for determining an anaerobic training effect in same terms.

Referring to FIG. 12 the exercise has six intervals during 16 minutes, each interval lasting about one minute. Intensity (% VO2 max), line 2 has been measured indirectly from heartbeat signal. External workload, here speed has been monitored by GPS. The ordinary intensity, line 2 gives quite a near repeating curve. Then measuring speed is much more challenging, when there are breaks in signal. Only the third interval has a clear curve of the speed corresponding to the actual workout. In all other intervals GPS-signal has been broken. However, whenever speed information is available, it may precede intensity data based on heart rate when calculating modified intensity. Thus, in the third interval the curves of speed and modified intensity coincide.

Figure 14:
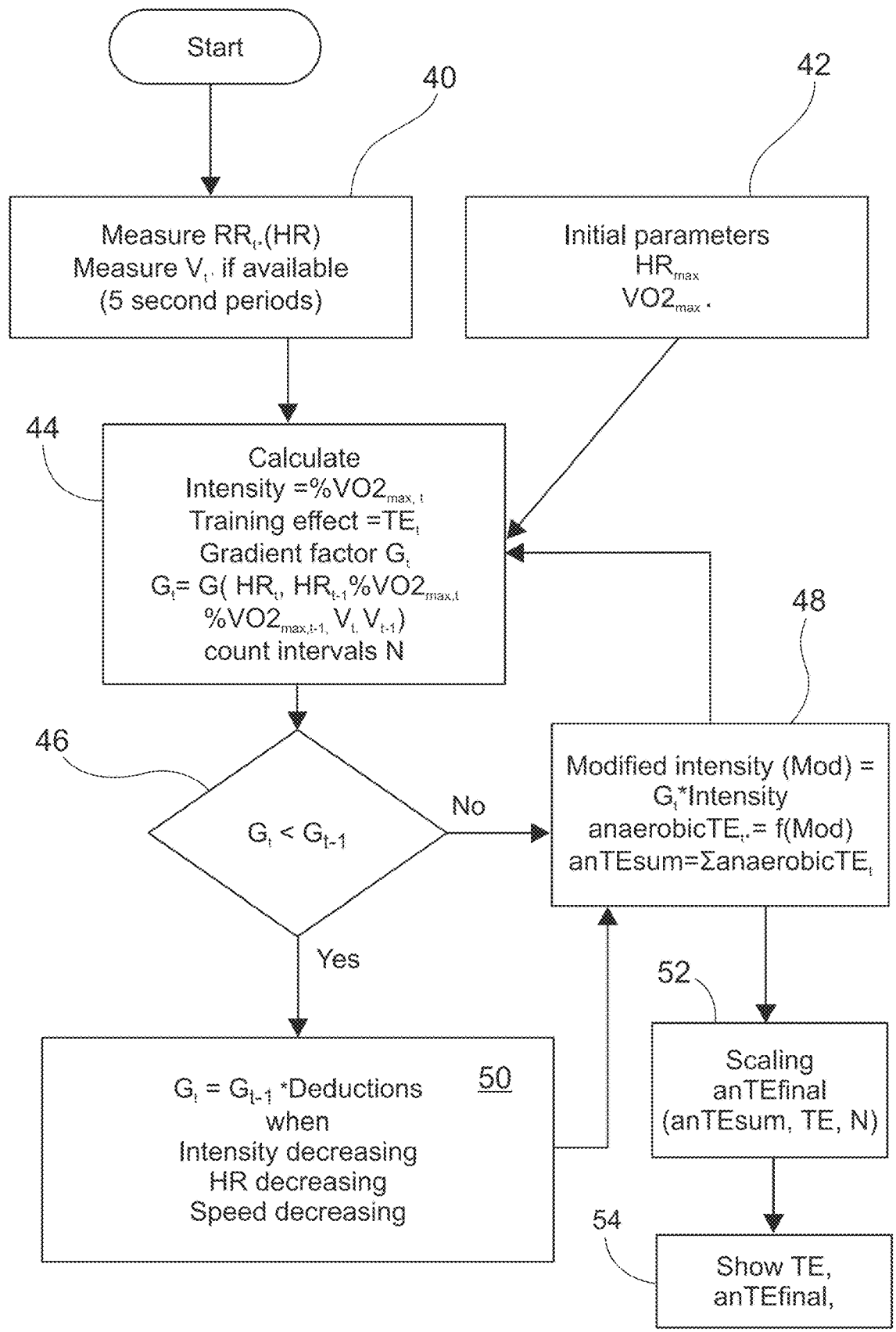
FIG. 14 represents an example of calculation of modified intensity with respect to how it may increase and decrease.

Another embodiment is shown in FIG. 14.

Figure 13:
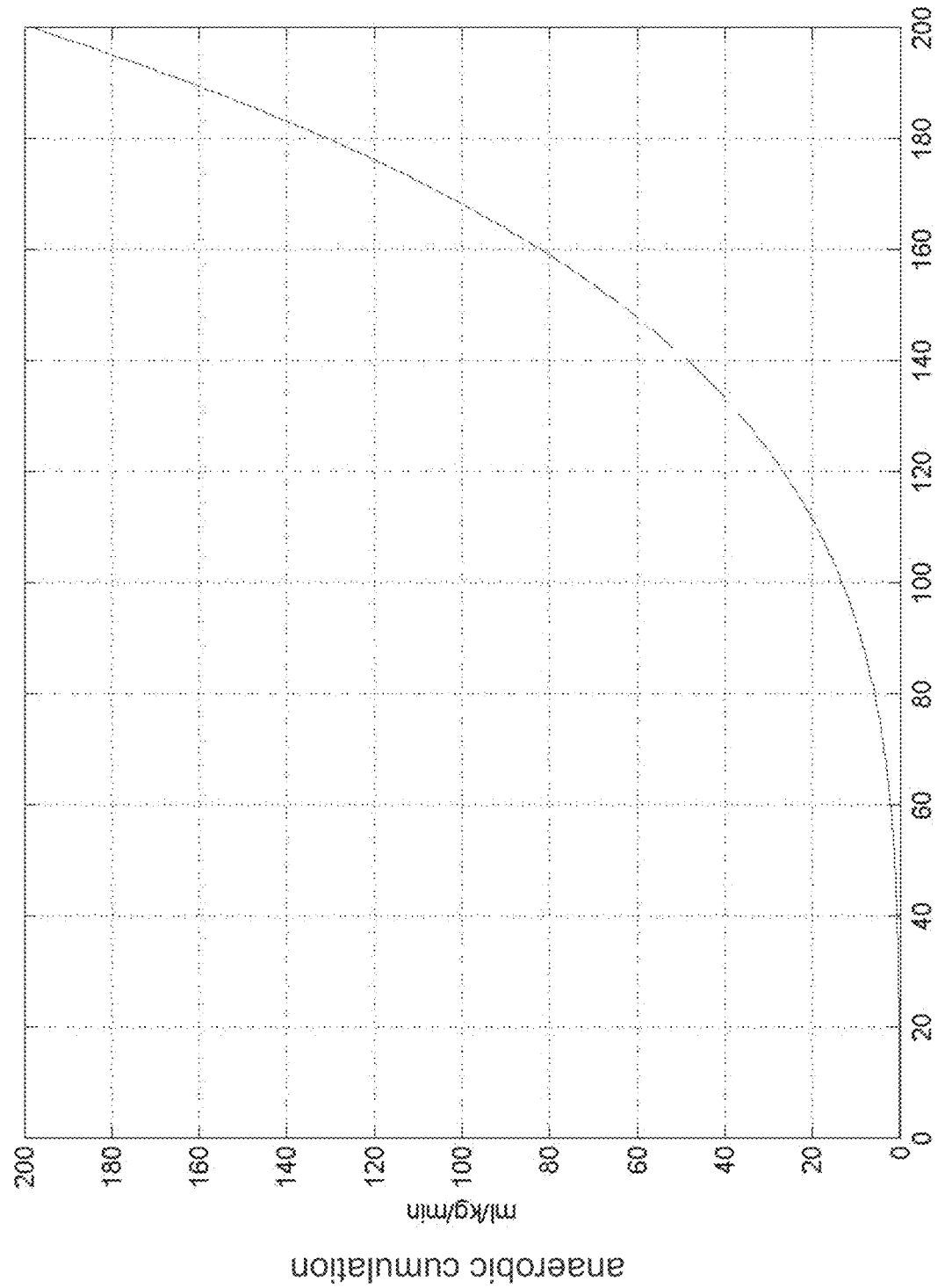
FIG. 13 represents an example of the accumulation of EPOC as a function of modified intensity.

Modified intensity is determined using an ordinary HR derived % VO2 max estimate, % HRmax and external workload after every 5 seconds with a range between e.g. 85-200%. Modified intensity is then converted to the accumulation of anaerobic training effect (anTE) using an empiric function shown graphically in FIG. 13. It counts the anTE adding each new value of a five second window to a sum, which presents a total anaerobic training effect, but without scaling. Generally, the calculation of modified intensity takes place in short periods of 2-20 seconds, while a 3-10 second period may be better.

The intelligence of the above described method is based on minimum information about characteristics of each interval and using just a calculation window without full history data of exercise. The characteristics of each interval is revealed just by a derivate of intensity and a starting level, and intensity change calculated preferably in a simple manner as a continuous average value. The full characteristics of each exercise interval are never revealed, but necessary information of each interval is obtained indirectly in a continuous calculation.

Referring to FIG. 14 heart rate (RRt) and external workload like speed V is measured periodically, e.g. in 5 second periods (generally 0.5-15 second, preferably 1-6 seconds). There is background information entered initially, particularly values depicting the maximum heart rate and the fitness level of the user, The modified intensity is determined by a multiplication of a factor $G_t$ and the measured intensity, i.e. the ordinary intensity. The factor $G_t$ is calculated continuously, and it has initial value of one as long as a gradient function yields a higher value over 1 (100%) using both the increasing gradient value and a starting level, step 44. The illustration of FIG. 14 is schematic. Artifact corrections are not presented. When the signal quality is weakening, the modified intensity is calculated more conservatively i.e. the factor G is reduced.

The level at which intensity ends up at any measurement point can be taken into account for example by using weights for multiplication of the actual gradient. A basic level of 50% yields weight of 0.35, 85% gives a weight of 1, 90% 1.12, and finally 100% level gives a weight of 1.4. A gradient value is easily obtained as a difference of two sequential values (time difference always 5 seconds). The weight is further multiplied by the MET—difference between current and previous measurement point. For example, if intensity ends up to 85% level and has increased by 2METs from previous point then G-value is 1.00×2=2.00.

A new value is calculated for the factor $G_t$ in every period (step 46). If the new value is bigger, an anaerobicTE-speed can be measured imminently, step 48. Otherwise there is a deduction process decrease the value of the factor G until it is one. The deduction are based on decreasing intensity, decreasing heart rate and/or decreasing external workload, step 50

Thus, another aspect is that factor G is kept up until it is gradually reduced due to several different factors like decreasing intensity (step 50), decreasing heart rate and/or decreasing external workload. Preferably speed or other power output is measured, when that information precedes heart rate based-intensity. After the deduction phase, step 50, the modified intensity (Mod) is calculated first in step 48. The function in FIG. 13 yields the accumulation speed of the anaerobic training effect, f(Mod), particularly its upslope component. Unscaled anaerobic training effect (anaerobic $TE_t$) is obtained by integrating all values to a sum. The recovery (a downslope component) is omitted and it can be handled in a similar manner as related to the aerobic TE (U.S. Pat. No. 7,192,401 B2) herein incorporated), if desired.

The "modified intensity" method according to FIG. 14 with recovery calculation (downslope component) has an advantage of simplicity, when the aerobic training effect is calculated using dependency between an intensity/oxygen consumption and EPOC. Now a special calculation of heart rate or measuring of external work load reveals actual and temporal oxygen requirement of exercise (theoretical VO2), which means that temporally physiological intensity (sum of aerobic and anaerobic energy yield) can be far over 100% VO2MAX—here limited TO 200% in this exemplary embodiment. Using same FIG. 13 (or similar chart) both aerobic intensity and anaerobic intensity can be converted to momentary EPOC ("oxygen debt")—values being so called upslope components. When downslope component is same for both, the overall calculation need relatively little resources in addition to the ordinary TE-calculation.

In order to standardize the result being compatible to different sport and different number of intervals, step 52, the result is scaled using also an ordinary training effect and the number of executed intervals. The scaling can be accomplished in many ways.

Finally the result is displayed in step 54, when both ordinary training effect and anaerobic training effect are shown in a display.

In one exemplary embodiment modified intensity is calculated as:

$$\text{modified intensity} = \text{Anaerobic Multiplier}(G) * \text{intensity}\_t, \text{ where}$$

$$\text{anaerobic multiplier}(Gt) = 1.3841 * \text{intensity}\_t^2 * (\text{MET}\_t - \text{MET}\_{t-1}) \text{ and intensity}\_t \text{ is provided as } \% \text{ VO2 max.}$$

The anaerobic multiplier (Gt) is based, in each period on final maximum intensity in selected power of range 1-4 (typically 2) and an increase of intensity within the period.

If external workload (Speed & altitude or power output) is recorded it may be heavily weighted in the calculation of modified intensity. In one exemplary embodiment modified intensity may be calculated solely based on external workload if following conditions are fulfilled: Anaerobic multiplier is greater than 1 and external workload is between 100 and 200% VO2 max.

In one exemplary embodiment modified intensity may be downgraded in cases when recorded intensity has been continuously high. For example in cases when intensity has not been under 70% VO2 max any time in preceding 5 min period. This rule may be used as a "sanity check" for the modified intensity especially in cases when external workload information is not available since it is impossible to perform significant amount of anaerobic work if there are no recovery breaks during in short term history.

A practical example of calculation of modified intensity and EPOC when external workload data is not available:

A Runner has VO2 max of 52.5 ml/kg min which is equivalent to 15 METs (=his VO2 max is 15-fold when compared to his expected resting VO2 of 3.5 ml/kg/min). The runner starts an exercise during which he runs 100 m repeats. In this example EPOC/TE accumulation is described in detail regarding the first repeat that lasts 15 seconds:

During the first 5 seconds ordinary heart rate based intensity increases from 30% VO2 max to 50%, which corresponds to an increase in METs from 4.5 to 7.5 MET. So the increase is 3METs and correspondingly
anaerobic multiplier (G)=1.3841*0.5^2*3=1.03
modified intensity=1.03*50% VO2 max=52% VO2 max
Because modified intensity is lower than 85%, 50% intensity is returned.
In this exemplary embodiment only intensities above 85% VO2 max are regarded meaningful in accumulating anaerobic training effect
anaerobic EPOC accumulates by 0.1002 ml/kg
aerobic EPOC accumulates by 0.1002 ml/kg During second 5 sec period intensity increase from 50% VO2 max to 70% VO2 max, which corresponds to an increase in METs from 7.5 to 10.5 MET. So the increase is 3 METs and correspondingly
Anaerobic multiplier=1.3841*0.7^2*3=2.03
modified intensity=2.03*70% VO2 max=142% VO2 max
anaerobic EPOC accumulates from 0.1002 ml/kg to 4.1352 ml/kg
aerobic EPOC accumulates from 0.1002 ml/kg to 0.3967 ml/kg During third 5 sec period intensity increases from 70% VO2 max to 80% VO2 max, which corresponds to an increase in METs from 10.5 to 12 METs. So the increase is 1.5 METs and correspondingly
anaerobic multiplier=1.3841*0.8^2*1.5=1.33
modified intensity=1.33*80% VO2 max=106% VO2 max
anaerobic EPOC accumulates from 4.1352 ml/kg to 5.5195 ml/kg
aerobic EPOC accumulates from 0.3967 ml/kg to 0.8738 ml/kg Total accumulated EPOCs are: anaerobic EPOC=5.5195 ml/kg/min, aerobic EPOC 0.8738 ml/kg/min. Difference is 4.6457 ml/kg/min which would mean accumulated anaerobic training effect value of 1.2 after the first repeat when runner's activity class is 7. When EPOC is used as an anaerobic sum measure scaling logic of FIG. 5 cannot be used as such. One suitable scaling logic is disclosed in patent publication U.S. Pat. No. 7,805,186 (B2) which presents an exemplary dependency between EPOC, activity class and Training effect.

In one exemplary embodiment, a method and system for detecting exercise intervals according to the present invention may include defining the interval-likeness of a time sequence of a physiological parameter, wherein the interval-likeness is proportional to at least some of the following properties of the time sequence: the time derivatives within the sequence, the local minima and maxima within the sequence, and the fluctuations within the sequence. A time sequence may then be regarded as an exercise interval if its interval-likeness value is higher than a predetermined threshold value.

In further exemplary embodiments, methods and systems for detecting exercise intervals, analyzing anaerobic exercise periods, and analyzing training effects may be described. A physiological response of a user may be continuously measured through one or more physiological parameters, wherein the physiological parameters may be recorded as physiological values. One or more high intensity intervals and non-interval periods may be identified based on a degree of change of one or more of the physiological values over a period of time. An anaerobic sum may be defined from at least one of: high intensity intervals and non-interval periods based on their properties. An anaerobic training effect may be determined based on anaerobic sum and a user's background parameters. The anaerobic training effect may be displayed to the user in comparison with calculated aerobic training effect.

As would be understood by a person of ordinary skill in the art, the training effect may be displayed in any manner as would be understood by a person or ordinary skill in the art. In further exemplary embodiments, the number of identified high intensity intervals, the duration of the intervals, or the like may be displayed to the user. In further exemplary embodiments, high intensity intervals may be classified and presented to a user according to predetermined criteria in any manner as would be understood in the art. In further exemplary embodiments, a description of the exercise and the physiological effect may be provided in any manner as would be understood by a person of ordinary skill in the art.

In further exemplary embodiments, methods and systems for analyzing anaerobic exercise periods, and analyzing training effects may be disclosed. A physiological response of a user may be continuously measured through one or more physiological parameters, wherein the physiological parameters may be recorded as physiological values. An external workload may be continuously measured wherein a plurality of measured workload values may be recorded and each measured workload value may be associated with one or more of the measured physiological values to form a plurality of data points. An aerobic training load may be calculated based on a measured physiological response. An anaerobic training load may be calculated based on measured external workload. A total training effect is determined using the higher training load value and one or more of user's background parameters, and determining anaerobic training effect as a relative value according to comparison between anaerobic training effect and total training effect.

In further exemplary embodiments, high intensity intervals may be identified based on at least one of: measured physiological response and measured external workload. The high intensity intervals may be classified based on predetermined criteria, and the number of identified high intensity intervals, duration of the intervals, and the classification of high intensity intervals may be displayed to the user. In further exemplary embodiments, a description of the exercise and the physiological effect may be provided in any manner as would be understood by a person of ordinary skill in the art.

In still further exemplary embodiments, methods and systems for detecting exercise intervals, analyzing anaerobic exercise periods, and analyzing training effects may be disclosed. A physiological response of a user may be continuously measured through one or more physiological parameters, wherein the physiological parameters may be recorded as physiological values. An external workload may be continuously measured, wherein measured workload values may be recorded and each measured workload value may be associated with one or more of the measured physiological values to form a plurality of data points. One or more high intensity intervals may be identified based on a degree of change of one or more of the physiological and/or external workload values over a period of time. One or more identified high intensity intervals may be determined to be an anaerobic interval based on one or more factors. An anaerobic sum of the one or more anaerobic intervals may be determined, and anaerobic training effect may be determined by comparing the anaerobic sum with an anaerobic work scale.

In still further exemplary embodiments, methods and systems for detecting exercise intervals, analyzing anaerobic exercise periods, and analyzing training effects may be disclosed. A physiological response of a user may be continuously measured through a plurality of physiological parameters, wherein the plurality of physiological parameters may be recorded as physiological values. An external workload may be continuously measured, wherein a plurality of measured workload values may be recorded, and each measured workload value may be associated with one or more of the measured physiological values to form a plurality of data points. One or more data points may be filtered based on predetermined criteria to form a plurality of accepted data points. One or more high intensity intervals may be identified based on a degree of change of one or more of the physiological or external workload values over a period of time. A probability that the one or more identified high intensity intervals is an anaerobic interval may be calculated based on one or more factors. The one or more high intensity intervals may be classified as an anaerobic interval if the calculated probability is above a predetermined threshold. An anaerobic sum of the one or more anaerobic intervals and the anaerobic sum of non-interval periods may be defined. An aerobic sum of the aerobic intervals may also be defined. Anaerobic training effect may be determined by comparing the anaerobic sum with an anaerobic work scale and an aerobic training effect may be determined by comparing aerobic sum with aerobic work scale. A total training effect may be determined as being the higher training effect value, and a ratio between the anaerobic training effect and the aerobic training effect may be determined, the ratio may represent the proportional benefit of exercise on, for example, energy production pathways.

A singular training effect values for each individual workout may only tell the immediate effect of one particular workout. That particular effect is limited to a numerical value, showing that it was an easier or harder aerobic or anaerobic activity. While it is advantageous to be able to distinguish between aerobic and anaerobic workouts, there are, however, further dimensions to aerobic and anaerobic activity.

An aerobic activity that achieves a high training effect value may be achieved by performing a long, low intensity aerobic activity or may also be achieve by performing shorter, high-intensity aerobic VO2Max intervals. In which case, it is helpful to further understand the exact type of workout being performed, based not only on training effect but on other unique characteristics of a workout. Similarly, a very intense anaerobic workout may focus on pure anaerobic power, which may be characterized by short bursts of activity with long rest, or on anaerobic capacity, using workouts that feature relatively shorter rest.

Possessing this kind of information may assist exercisers in better understanding the specific type of fitness each workout may have improved. Over a longer term, it would also be possible to see the distribution of the different types of training and to know if there has been adequate balance between the various types of training or whether a specific dimension of fitness has received sufficient attention.

Furthermore, information about the training intensity distribution (training load distribution) can be used to help a user to better understand his/her current training status. (See applicants' prior patent applications US2018/0174685A1 and US2018/0310874A1). For example, if a user's training load is moderate but fitness level is declining, the user's training status may be determined to be "Unproductive". By analyzing the activity history and determining training load distribution the reason behind "unproductive" status may be solved. If the training history shows a clear shortage in aerobic low intensity training, it would be easy to tell the user e.g. "'Unproductive'—High relative amount of high intensity training may have turned your training status into Unproductive. Increase aerobic low intensity training to get Productive again". If information about training load distribution would not be analyzed at all, there would also be likelihood that an evaluation is made that the quality of training has been OK and that declining fitness level may be caused by poor recovery induced by poor nutrition, poor sleep, excess stress or illness. On the other hand, the above example history data analysis may also show a good balance in terms of training intensities in which case user should be instructed to check his/her other living habits or health status as they would then be the likely reasons behind poor fitness development. In other words, the current method enables, for example, a fitness device to automatically exclude certain reasons and thus enable more accurate instructions for future. Of course, in the above example history data analysis may also show a good balance in terms of training intensities in which case user should be instructed to check his/her other living habits or health status.

In an exemplary embodiment, a method may be used to provide additional feedback on the specific benefit of each exercise session. The results of the workout may be supplemented by additional feedback beyond showing a singular training effect value. The additional feedback, which may be referred to as a "training label", may be determined using the steps shown in FIGS. 17-19. A first part of the process, as described previously, is to determine a numerical value of training effect, for both an aerobic training effect and anaerobic training effect.

In an exemplary embodiment, a determination of feedback phrase is made separately for both the aerobic training effect (FIGS. 18, 19, 21) and anaerobic training effect (FIGS. 15-17, 19).

Aerobic Feedback

Aerobic feedback phrases may be determined based on the aerobic training effect value and information on the intensity distribution of exercise. In running intensity distribution is analyzed in terms of heart rate and optionally running speed and in cycling in terms of heart rate and optionally cycling power (see FIG. 18).

As can be seen from FIG. 18, analysis of intensity distribution may be based on various factors related to the intensity a person exercises at and the length of time spent in certain intensity zones (in terms of, for example, heart rate, running speed, or cycling power), or the duration of the period of intensity relative to the total duration of the activity.

Intensity may be measured as a relative intensity, benchmarked against lactate threshold heart rate (LTHR) or lactate threshold speed (LT speed) or Functional Threshold Power (FTP) of the user. These measures may be manually input by the user or automatically calculated based on earlier workouts. If the values are not known by other means, they may also be estimated using the following formulas:

In an alternative embodiment, the results of the workout may be supplemented by additional feedback beyond showing training effect, and is described in several steps below.

Showing a numerical value of training effect value for:

a) Aerobic training Effect b) Anaerobic Training Effect

Determining and showing feedback phrases related to both aerobic and anaerobic work to the user (FIG. 15-21).

Figure 19:
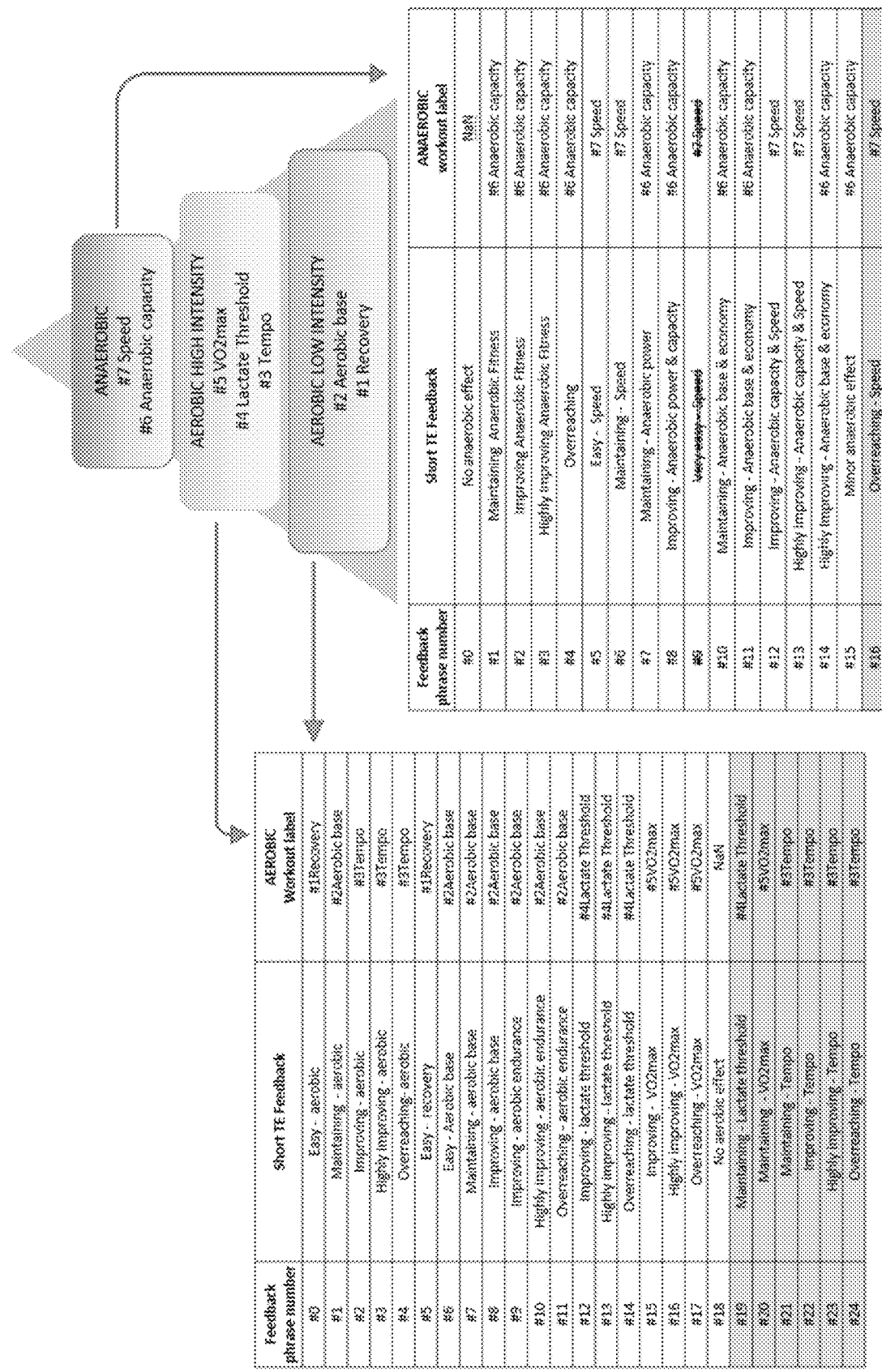
FIG. 19 represents an example selection logic for determining the aerobic and anaerobic workout label for each activity

Aerobic Feedback phrase telling the aerobic benefit of workout (FIGS. 18, & 19 and 21). Aerobic feedback phrases may be determined initially based on the aerobic training effect value, and may additionally be chosen based on extended criteria. Extended criteria is based on relative intensity wherein the intensity is benchmarked against lactate threshold heart rate (LTHR) or lactate threshold speed (LT speed) or Functional Threshold Power (FTP) of the user, and examples of said criteria are shown in FIG. 18. In cases where these values are not known they may be estimated using the following formulas $$\text{Est. FTP power (W)} = ((\text{maxMET} * 3.5 * \text{weight} - 350)/12.24) * 0.828$$

$$\text{Est. LT speed (m/s)} = (\text{maxMET} * 3.5 - 3.5)/12 * 0.828 + 0.1486$$

If LTHR not known, use default 90% Hrmax as LTHR where maxMET may be determined based on a user's fitness level, or VO2Max.

Some of the criteria may also be based on the corresponding anaerobic training effect value.

FIG. 17 (corresponding to Table 5-1) presents an example table of an alternative embodiment for the selection of anaerobic feedback and FIG. 18 (corresponding to Table 5-2) presents an example table of an alternative embodiment for the selection of aerobic feedback.

TABLE 5-1

ANAEROBIC FEEDBACK PHRASE LOGIC

|  | Other Conditions | Anaerobic TE | | | | | |
|---|---|---|---|---|---|---|---|
|  |  | 0-0.9 | 1.0-1.9 | 2.0-2.9 | 3.0-3.9 | 4.0-4.9 | 5.0 |
|  |  | Only anaerobic phrases 0-4 and 15 are possible when "gym" flag is selected for a workout<br>Other rules related to use of ETE library:<br>Speed inputted to ETE only in running exercises.<br>Power inputtted to ETE only in cycling workouts | | | | | |
| Power | No other conditions | #0 | #15 | #1 | #2 | #3 | #4 |
| c1 Speed | Peak modified intensity >140% in 5 or more repeats (scale 12-17MET => 150%-130%) AND each repeat lasting 20 sec or less | #0 | #5 | #6 | #12 | #13 | #4 |
| c2 Power | Average mod intensity >115% for a total of 75 sec or more AND in 3 or more repeats AND each repeat lasting 10 sec or more (scale 12-17MET => 120%-110%) | #0 | #15 | #7 | #8 | #3 | #4 |
| c3 Power | Average mod intensity >95% for a total of 150 sec or more AND in 7 or more repeats (scale 12-17MET => 100%-95%) AND each repeat lasting 20 sec or more AND aerTE < 4.0 | #0 | #15 | #10 | #11 | #14 | #4 |

TABLE 5-2

AEROBIC FEEDBACK PHRASE LOGIC

|  | Other conditions | Aerobic TE | | | | | | | | |
|---|---|---|---|---|---|---|---|---|---|---|
|  |  | 0-0.9 | 1 | 1.5 | 2 | 2.5 | 3 | 3.5 | 4 | 4.5 | 5 |
|  |  |  |  | z | z |  | z | z |  |  |  |
| Recovery/ Tempo | No other conditions | #18 | #0 |  | #1 | #2 |  | #3 |  | #4 |
| c1: Recovery/ Tempo | 10 min ≤ Duration ≤ 40 min AND anTE < 1.0 | #18 | #5 |  | #1 | #2 |  | #3 |  | #4 |
| c2: Recovery/ Base | Duration > 40 min AND Time in HR zone > 95% LTHR for less than 8% of total duration AND C4t2 + C5t2 less than 15% of total duration AND anTE < 4.0 AND time at 61-92% LTHR > 35 min | #18 | #0 | #6 | #7 | #8 | #9 | #10 | #11 |
| c3:Recovery/ Tempo | Cumulative time<br>1. @ HR zone 90-96% LTHR equal to or more than 16-24 min AND cumulative time equal to or more than 20% of total exercise time<br>2. OR ETEspeed @ 90-96% of AnT speed ≥ 16-24 min AND cumulative time equal to or more than 22% of total exercise time<br>3. OR 30 sec_avg_power @ 76-92% of Antpower) ≥ 24-32 min AND "interval not detected" AND cumulative time equal to or more than 25% of total exercise time AND anTE < 4.0 | #18 | #0 |  | #21 | #22 |  | #23 |  | #24 |
| c4: Recovery/ LT | Cumulative time<br>1. @ 94-102% LTHR AND @ modified intensity < 95% VO2max equal to or more than 10-15 min AND cumulative time equal to or more than 15% of total exercise time<br>OR<br>2 @ ETEspeed 94-105% of AnT speed equal to or more than 10-15 min AND cumulative time equal to or more than 15% of total exercise time<br>OR<br>3. @ 30 sec_avg_power 90-105% of AnT power equal to or more than 13-18 min AND "interval not detected" AND cumulative time equal to or more than 20% of total exercise time AND anTE < 4.0 | #18 | #0 |  | #19 | #12 |  | #13 |  | #14 |

TABLE 5-2-continued

AEROBIC FEEDBACK PHRASE LOGIC

| | | Aerobic TE | | | | | | | | | |
|---|---|---|---|---|---|---|---|---|---|---|---|
| | Other conditions | 0-0.9 | 1 | 1.5 | 2 | 2.5 | 3 | 3.5 | 4 | 4.5 | 5 |
| c5 Recovery/ VO2max | If duration ≥ 5 min ARD cumulative time at one of the zones (see below: either based on % LTHR or % ETEspeed or % AnT power) in zone greater than 8 min or more than 80% of total duration else if Cumulative time 1. @ ≥ 100% LTHR AND modified intensity ≤ 100% equal to or more than 6-12 min OR 2. @ ETEspeed ≥ 102% of AnT speed AND modified intensity ≤ 103% equal to or more than 8-12 min min AND cumulative time equal to or more than 10% of total exercise time OR 3. @ 30 sec_avg_power higher than 102% of AnT power AND smaller than 127% of AnT powr equal to or more than 8-12 min AND "interval not detected" AND cumulative time equal to or more than 15% of total exercise time | #18 | #0 | | #20 | | #15 | | | #16 | #17 |

Example Cases According to Tables 5-1 and 5-2

A cyclist (AC8) performs a workout consisting of a variable intensity warm-up, 2×20 min repeats at an intensity close to or above his lactate threshold (FTP) intensity and a short cool-down. During a warm-up his intensity is mostly lowish staying mostly below 90% LTHR and below 76% FTP. During the latter part of warm up his intensity increases above 76% FTP but that does not yet raise aerobic TE to 2.0. Since time at recovery and base training zones (=61-92% HRmax) does not accumulate above the 35 min threshold, and short recovery does not accumulate much time at Tempo zone or higher zones either, aerobic feedback phrase changes from #18 (no aerobic effect) into #5 (Easy recovery). At that time point no anaerobic training effect has yet accumulated and thus anaerobic feedback phrase stays at #0 (no anaerobic effect). Thus the primary benefit after the warm-up is #1—"Recovery". After a few minutes of first FTP-power repeat, while the aerobic TE reached the level of 2.0, aerobic feedback phrase turns into #1 (Maintaining aerobic) which triggers also the change of primary label into "Aerobic base" since the exercise has still accumulated very little of high intensity effort when compared to total working time (35 min) so far. Also the anaerobic TE is still 0.0 at that point. However, about 5 minutes later, when repeat has taken approx. 8 min Aerobic TE reaches 3.0 level and accumulated time at 61-92% HRmax-intensity is less than 35 min. Aerobic feedback phrase #8 is thus not possible and aerobic feedback phrase turns into #2 ("Improving Aerobic") which in turn changes primary label from "Base" into "Tempo" since anaerobic TE is still 0.0. At the end part of first 20 min repeat the cyclist has accumulated enough time (13 min 20 sec) considering his activity class at lactate threshold HR zone (94-102% LTHR) without modified intensity simultaneously reaching too high values (>95%). Accordingly, aerobic feedback phrase changes into #12—"Improving lactate threshold" which also causes the primary label to turn into #4—"Lactate Threshold". After a short recovery period the user starts his second repeat where the intensity is slightly higher when compared to the first one. During the second repeat aerobic feedback phrase turns into #13—"Highly improving lactate threshold" but it does not cause changes in primary label. Due to the increased effort time at VO2 max training zone starts to accumulate. Also, the anaerobic training effect is starting to increase. At the very end of $2^{nd}$ repeat user reaches a trigger limit which is 10 min 30 sec at VO2 max HR zone. Accordingly, aerobic feedback phrase turn into #16—"Highly improving VO2 max". In the comparison of aerobic training effect (4.5) and anaerobic training effect (3.5) aerobic energy systems are regarded as the main beneficiary. Accordingly, primary label (primary benefit) at the end of workout is #5 (VO2 max)—not anaerobic capacity even though the anaerobic work of workout has focused on that ability. All aerobic load of that exercise (208 units) is allocated to "VO2 max"-label and "Aerobic high" category. All anaerobic load (116 units) is allocated to "Anaerobic" intensity category since the workout exceeded anTE 1.0 level. Anaerobic load is further allocated under "anaerobic capacity" label since detected supramaximal effort did not reach high enough level in order to be regarded as speed training (Anaerobic feedback phrase=#2).

Anaerobic Feedback

Anaerobic feedback phrases tell the anaerobic benefit of workout, examples of the feedback are shown in FIGS. 17, 19, and 20. Feedback phrases may be determined using the determined anaerobic training effect, in addition to criteria related to modified intensity measurements as well as quantity, duration, and intensity of detected anaerobic intervals. This may also include external workload intensity, such as based on speed from running workouts or power input from cycling workouts.

Summary Feedback

Based on both the aerobic and anaerobic feedback phrases determined for each exercise, a summary of the current training session may be determined by means of workout labels. The purpose of labels is to summarize the benefits of workout with respect to the physiological systems developed. Aerobic workout labels 1-5, comprise for example, recovery training, aerobic base training, tempo training, lactate threshold training and VO2 max training. Anaerobic training labels 6-7, comprise for example anaerobic capacity training or speed training.

Summarizing the current training session by determining all of the benefits (=load for 1 or more workout labels) of said training session
   a. For aerobic energy production
      i. Workout labels 1-5 (FIG. 19) comprising, for example, recovery training, aerobic base training, tempo training, LT training and VO2 max training)
   b. For anaerobic energy production (labels 6-7) (See FIG. 19)
      i. Comprising e.g. anaerobic capacity training and speed training In one exemplary embodiment presented in FIG. 19 each workout may get two labels (meaning two main benefits): 1) one of the aerobic low or aerobic high intensities comprising labels #1-#5 and 2) either one of the anaerobic labels #6-#7. For example, an easy jogging workout including ten 50 m sprints may get label 2 ("Base") from the aerobic labels and label 7 "Sprint" from the anaerobic labels.

Determining and showing the primary benefit (primary label) of workout. From a coaching point of view it is often useful to also point out the primary label (=primary benefit) of each workout. The selection of the primary label of the workout may be performed based on the calculated aerobic and anaerobic training effect using for example the following criteria:
   When anaerobic TE (anTE)≥3.0, select anaerobic label (label 6 or 7) as the primary label if it is greater or equal to aerobic TE (aerTE)−0.5. If anTE<3.0, then the primary label is whichever is higher, aerobic (label 1, 2, 3, 4 or 5) or anaerobic TE.
   If anTE=aerTE then the Anaerobic effect is always selected as primary label
   If anaerobic label is SPEED AND anTE≥2.0, select anaerobic label as primary label label if it is greater or equal to aerobic TE−1. If anaerobic label is SPEED AND anTE<2.0, then the workout label is based on whichever training effect is higher, aerobic or anaerobic TE.
   In "strength training mode", select anaerobic label as workout label if AnTE≥1 if it is greater or equal to aerobic TE−1.5. "Strength training" is an example of a mode may be selected whenever user selects a sport mode for an exercise that is characterized by lifting weights or where user has to use high amount of force in short bouts.

There may optionally be presented a "secondary" label, which would be the training effect label that is not selected as the primary label.

Figure 22:
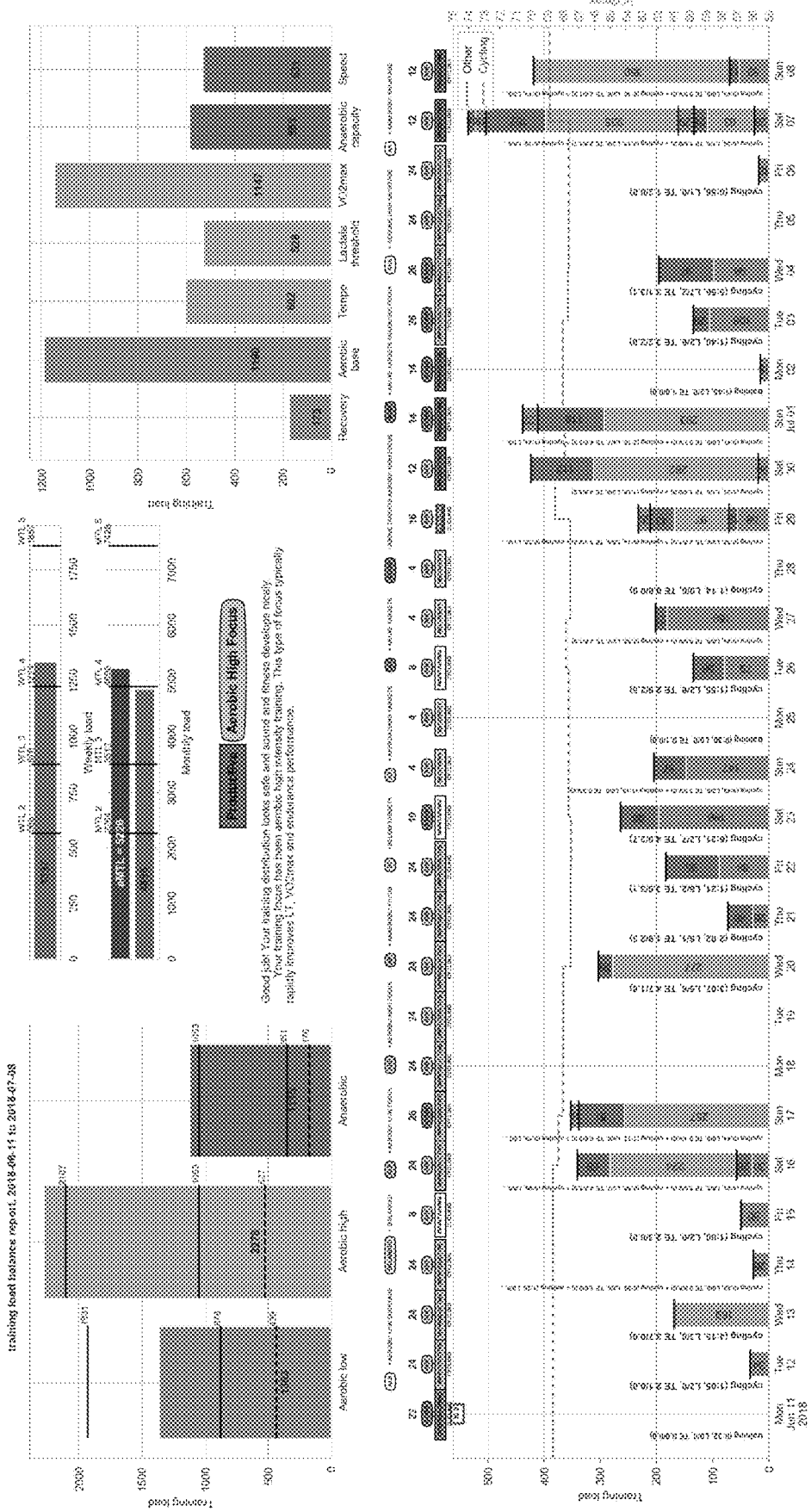
FIG. 22 displays an example user interface showing training load distribution FIG. 23 displays an example user watch-style device user interface showing workout result label feedback.

To illustrate the balance of a user's training, the training history may be summarized. In an exemplary embodiment, a summarized training history may comprise summing all of the training load accumulated and distributed to the different training labels. The training load is distributed unweighted, regardless of whether it has the "primary" or "secondary" training load (For example a training session with aerobic TE of 3.3 and anaerobic TE of 1.1 would get a primary label from some of the aerobic labels #1-#5. Regardless of that also the secondary anaerobic effect #6 or #7 would be taken into account in load distribution). Any duration of historical training load may be presented to the user. FIG. 22 shows an example of cumulative training load feedback. As shown in FIG. 22, historical training load may be shown in a daily calendar, a weekly (7-day) illustration, a monthly (28-day) illustration, a custom date as specified by the user, or even a yearly (365-day) distribution (not shown). Load distribution may also be shown per each label or alternatively by diving labels e.g. into 3 groups (as shown in FIG. 19): Labels 1-2 to "Aerobic low intensity" category, labels 3-5 to "Aerobic High Intensity" category and labels 6-7 to "Anaerobic intensity" category.

The purpose of calculating the intensity-based load distribution is to track whether a person is sufficiently stressing different body systems.

In a specific situation, where feedback phrase number 0, with the workload label of NaN as shown on FIG. 20 may not be taken into account in training load distribution.

Historical training load distribution may be calculated using a different software library (in this case Training History Analysis—THA library) than the library that calculates aerobic and anaerobic TE values, feedback phrases and workout labels for a specific workout. This may help in saving computational power as these calculation processes need not be performed at regular intervals (e.g. 5 sec intervals) but instead, may be calculated only after a new exercise session or in the beginning of a new day.

It is also possible to combine training status to training load distribution feedback (also referred to as training load balance feedback). This feedback logic is also described below.

Training Load Distribution

To summarize training history in a more simplified manner, the distribution of training load may be placed into intensity categories. Training load may be divided into three intensity categories (Aerobic Low, Aerobic High and Anaerobic) based on the workout label of each exercise. Aerobic low may generally be defined as low-intensity aerobic training, for example, aerobic exercise at a heart rate below 80% of a person's maximum heart rate. This kind of training forms the basis of any endurance training plan as this type of training allows high training volumes. Aerobic high would then be considered exercise that involves a higher heart rate than the defined intensity threshold of aerobic low, but does not belong in the category of being an anaerobic exercise, anaerobic exercise being identified, for example, by the method described above. Aerobic high training intensities can be used to optimize aerobic capacity. However, regardless of being efficient in optimizing aerobic (cardiorespiratory) capacity this kind of training increase training load rapidly and can thus not be repeated as often as aerobic base workouts. Accordingly, Aerobic Low intensity training allows training on a daily basis (or even several daily workouts) in long term which is why this type of training forms the basis of endurance training. Anaerobic training is performed at intensities beyond a person's VO2 max. They are needed to optimize performance as this kind of training improves, for example, exercise economy, as well as capability to (repeated) sprints which are crucial characteristics in endurance sports.

Accordingly, all training intensities have are relevant when it comes to development and optimization of endurance performance.

In addition to load sums for each intensity category, the THA library may also calculate load target areas for each intensity category, as shown in FIG. 22.

Exemplary cumulative load targets per each intensity category shown in FIG. 22 may be determined for example using an athlete database wherein the limits are based on averages and standard deviations observed in subgroup of athletes whose fitness level has been developing faster than group average. The limits may also take into account user's activity class and are described in more detail below.

The feedback presented to a user may be presented on the apparatus described earlier and shown in FIG. 11. This feedback may be, for example, based on the realized training load of the training history as compared to the training load target values for each of the aforementioned categories. In addition to the graphical information shown, additional feedback phrases and sentences, as shown in tables 8 and 9 below may be presented to the user on the selected apparatus.

Activity Class

"Basic" AC (Basic Activity Class)

The activity class refers to a general descriptor of a person's fitness level, activity history or training history. The present activity class may be evaluated using background information, such as age, gender, a fitness level (e.g. a maximum oxygen consumption value, VO2 max) and/or training history data. A target exertion level for each planned exercise is determined individually for each person. The target exertion level of a user may be determined based on maximum heart rate (maxHR), of a user, which may be determined based on age, which is received as a background information. Other background information may also have an effect on the determination of an exertion level of a user. For example, fitness level may be estimated using background information optionally in combination with training history. Resulting fitness level may be used to determine target velocity, pace or power for different workouts. In a case where a user has performed exercise(s) by recording heart rate (HR) and positions, e.g. GPS positions; or HR and external power, it is possible to determine fitness level more accurately and thus the accuracy of target speeds and/or powers for workouts is determined more accurately correspondingly. Fitness level may be determined as described in U.S. Pat. No. 9,237,868 and U.S. Ser. No. 10/123,730. Further, other measured, calculated, detected or estimated values may have effect on the determination of an exertion level of a user. Measured values may comprise heart rate and heart rate variability (HRV) of the user. Thus, training history of a user, if available, may comprise information that has an effect on prescribed exertion level of a user. An activity class classification may comprise a scale, e.g. of 0-10, wherein 0 represents a sedentary person, while 10 represents highly fit/trained user, who exercises regularly. Each activity class has its own specific training load target. The training load target may comprise a range. The training load target comprises a lowest limit for a training load of the activity class. In addition, the training load target may comprise an upper limit for a training load of the activity class.

Person's training tolerance may, for example, be determined based on monthly training load (28 day training load sum=monthly training load=MTL), VO2 max, gender and age where age and gender can be used to classify the VO2 max value. Training load and VO2 max may have separate criteria and basic AC may be determined as a maximum of these two (see FIG. 25). For example, a 40 year old man with VO2 max of 45 ml/kg/min and MTL of 1600 would get an activity class of 6 based on his VO2 max and activity class of 8 based on MTL value. Thus his final "basic" activity class would be 8.

Averaged Activity Class (aAC):

The training load target values for each category may be based on an averaged activity class (aAC) which is more stable compared to only "basic" AC. Using only AC could lead to a "moving goalposts" issue, where a user who tries to balance their training load ends up in a different activity class with different MTL limits, and further away from balance. For example, a user with a shortage of anaerobic training could try to reach balance by doing a hard anaerobic workout, and this workout could then push the user to a higher AC and result in a shortage of aerobic load.

Similar to basic AC, aAC is a maximum of a VO2 max-based value, a monthly (28-day) load-based value, and an activity class constant such as 4.0. However, to make aAC less sensitive to changes in the short-term training load, the monthly load is calculated as a weighted sum that puts emphasis on how the user trained approximately a month ago. This averaged monthly training load (aMTL) is calculated as follows:

1. Compute the daily average training load of the user as a weighted average where each workout is weighted depending on its age as shown in the table below (exercises on the current day and 6 preceding days get a weight of 1, exercises in the preceding 7 day period get a weight of 2, etc).
2. Scale the daily average training load to a monthly aMTL as in the usual MTL (If the known training history spans N≤6 days, multiply by 4*N, otherwise multiply by 28).

Computed this way, aMTL is approximately equal to an arithmetic average of MTL as computed 0, 1, 2, 3, and 4 weeks ago.

By way of example, similar to basic AC, if 40-year-old man with 45 ml/kg/min VO2 max was able to achieve aMTL of 1600 units, also his aAC would then be 8. However, it is somewhat harder to reach 1600 units of aMTL when compared to 1600 units of MTL

TABLE 7

Weighting of training load based on the date of exercise relative to current date.

| Age of exercise (days) | Weight |
|---|---|
| 0-6 | 1 |
| 7-13 | 2 |
| 14-20 | 3 |
| 21-34 | 4 |
| 35-41 | 3 |
| 42-48 | 2 |
| 49-55 | 1 |
| 56- | 0 |

Target behavior in aAC is to show load target level that has been suitable target for the user during last month; i.e what user has been seeing as the target weekly load during past month. It is thus changing more slowly than "basic" AC meaning that "basic" AC may now have harder requirements to the user for the coming week than what is the requirement for the past months training.

Determination of Training Load Targets, Based on Activity Class

Activity class (AC)-based target values for monthly training load (MTL) are determined for each category. As a general rule of thumb: training is in good balance when load in each category is within their target limits.

During an early phase of the training when the user has not yet trained for a full month (28 days) or there is not enough training data history, the target values shown below in table 6 are multiplied with L/28, where L<28 is the number of days from the oldest recorded exercise to the current date.

TABLE 6

Sample training load target values

| TARGET VALUES | Aerobic Low | Aerobic High | Anaerobic |
|---|---|---|---|
| Minimal limit | 12.5% of MTL 3.0 | 15% of MTL 3.0 | 5% of MTL 3.0* |
| Target lower limit | 25% of MTL 3.0 | 30% of MTL 3.0 | 10% of MTL 3.0* |
| Target upper limit | 55% of MTL 3.0 | 60% of MTL 3.0 | 30% of MTL 3.0 |
| Very high limit | 80% of MTL 3.0 | 80% of MTL 3.0 | 60% of MTL 3.0 |

MTL limits always determined based on monthly average activity class (aAC)
*IF AC ≤ 7 minimal limit AND target lower limit for anaerobic is 0

Training Distribution Feedback

Based on the actual accumulated load and its distribution, exemplary feedback sentences are provided according to the rules described in the below tables 8 and 9.

There are some potential exceptions to the rules shown below:

Below targets: Monthly load is under 65% of MTL 3.0 (this value is scaled during the onboarding phase like other training load target values)

"Approaching targets" is provided instead of below targets if WTL≥2.5

Above targets: 145% or higher of MTL 3.0 (this value is intentionally not scaled during the onboarding phase)

Focus is selected for that category which is proportionally closest to "upper-limit" or "very high limit"

Additional exceptions would be to not allow 1) "Above targets" NOR 2) "Approaching targets" if the below table suggests "#2 Aer. low Shortage" (I.e. Then show "#2 Aer. low Shortage" to a user)

TABLE 8

| # | Distribution feedback | Example of long feedback |
|---|---|---|
| 0 | No result | |
| 1 | Below Targets | "Your long term training load is below optimal. Increase training load" **Rule: Monthly load is under 65% of MTL 3.0 |
| 2 | Aerobic Low Shortage | "Total amount of high intensity training is too high with respect to amount of low intensity training. Increase amount of low intensity training to get your training into better balance and to develop performance optimally" |
| 3 | Aerobic High Shortage | "Proportion of aerobic high intensity training has been very low during past 4 week period. Training may not therefore develop aerobic capacity (LT/VO2max) optimally" |
| 4 | Anaerobic Shortage | "Proportion of anaerobic high intensity training has been very low during past 4 week period. As variation in training stimuli per se and impact for anaerobic capacity and speed has been too low - training benefits is expected to be suboptimal" |
| 5 | Balanced | "Your training is in good balance thus expectedly resulting in comprehensive benefit for all areas of fitness" |
| 6 | Aerobic Low Focus | "Your training focus has been in aerobic low intensity training. This type of focus builds foundation for sustaining harder training periods." |
| 7 | Aerobic High Focus | "Your training focus has been aerobic high intensity training. This type of focus typically rapidly improves LT, VO2max and endurance performance." |
| 8 | Anaerobic Focus | "Your training focus has been anaerobic high intensity training. This type of focus maximizes endurance performance rapidly. Notice that your body needs aerobic training focus after this kind of training period". |
| 9 | Above targets, Aer. Low Focus | Your training load is high. Remember to include lighter training periods to your training schedule. **Rule: Focus is selected for that category which is proportionally closest to "upper-limit" or "very high limit". |
| 10 | Above targets, Aer. High Focus | |
| 11 | Above targets, Anaerobic Focus | |
| 12 | Approaching targets** | "Your long term training load is below optimal but is moving towards targets" **Rule: "Approaching target" is provided instead if "below targets" if WTL ≥ 2.5 |

It may be considered obvious to a man skilled in art that the table above could be modified in scope of this invention. For example, Distribution feedbacks #0-8 could form a basic set of feedbacks. Additionally, feedbacks 9-11 could be combined under a generic "Above targets" feedback. Furthermore, feedback #12 "Approaching targets" can be included if a more positive "tone of voice" is preferred instead of corrective feedback.

Table 9 shows the feedback phrase selection logic based on the relationship between aerobic training load and its related training limits, and the anaerobic training load and its related training limits.

In addition to the typical feedback, some cells in the below table 9 include additional feedback, specifically "(Below targets)" and "(Above targets)". These references may be optionally used to overrule the primary feedback based on the MTL based rules presented in the prior table. Hence, in certain situations, an additional feedback or rule may be included to overrule the initial rule in particular circumstances.

TABLE 9

TRAINING LOAD DISTRIBUTION FEEDBACK PHRASE LOGIC

| | Aer. High below minimal limit | Aer. High below target | Aer. High in target | Aer. High above target | Aer High above Very high limit |
|---|---|---|---|---|---|
| Aer. low below minimal limit | | | | | |
| Anaerobic below minimal limit | #5 Balanced (#1 Below targets) | #2 Aer. Low Shortage (#1 Below targets) | #2 Aer. low shortage (#1 Below targets) | #2 Aer. low shortage | #2 Aer. low shortage |
| Anaerobic below target | #2 Aer. Low Shortage (#1 Below targets) | #2 Aer. Low Shortage (#1 Below targets) | #2 Aer. low shortage | #2 Aer. low shortage | # 2 Aer. low shortage |
| Anaerobic in target | #2 Aer. Low Shortage (#1 Below targets) | #2 Aer. low shortage | #2 Aer. low shortage | #2 Aer. low shortage | #2 Aer. low shortage |
| Anaerobic above target | #2 Aer. low shortage (#1 Below targets) | #2 Aer. low shortage | #2 Aer. low shortage | #2 Aer. low shortage | #2 Aer. low shortage |
| Anaerobic above very high limit | #2 Aer. low shortage | #2 Aer. low shortage | #2 Aer. low shortage | #2 Aer. low shortage | #2 Aer. low shortage (Above targets) |
| Aer. low below target | | | | | |
| Anaerobic below minimal limit | #6 Aer. Low Focus (#1 Below targets) | #5 Balanced (#1 Below targets) | #4 Anaerobic Shortage | #2 Aer. low shortage | #2 Aer. low shortage |
| Anaerobic below target | #5 Balanced (#1 Below targets) | #2 Aer. Low Shortage (#1 Below targets) | #2 Aer. low shortage | #2 Aer. low shortage | #2 Aer. low shortage |
| Anaerobic in target | #3 Aer. high Shortage (#1 Below targets) | #2 Aer. low shortage | #2 Aer. low shortage | #2 Aer. low shortage | #2 Aer. low shortage |
| Anaerobic above target | #3 Aer. high Shortage | #2 Aer. low shortage | #2 Aer. low shortage | #2 Aer. low shortage | #2 Aer. low shortage |
| Anaerobic above very high limit | #3 Aer. high Shortage | #2 Aer. low shortage | #2 Aer. low shortage | #2 Aer. low shortage | #2 Aer. low shortage (Above targets) |
| Aer. low in target | | | | | |
| Anaerobic below minimal limit | #3 Aer. high Shortage (#1 Below targets) | #4 Anaerobic Shortage (#1 Below targets) | #4 Anaerobic Shortage | #4 Anaerobic Shortage | #4 Anaerobic Shortage |
| Anaerobic below target | #3 Aer. high Shortage (#1 Below targets) | #3 Aer. high Shortage | #5 Balanced | #7 Aer. High Focus | #7 Aer. High Focus |
| Anaerobic in target | #3 Aer. high Shortage | #5 Balanced | #5 Balanced | #7 Aer. High Focus | #7 Aer. High Focus |
| Anaerobic above target | #3 Aer. high Shortage | #8 Anaerobic Focus | #8 Anaerobic Focus | #7 Aer. High Focus | #7 Aer. High Focus (Above targets) |
| Anaerobic above very high limit | #3 Aer. high Shortage | #8 Anaerobic Focus | #8 Anaerobic Focus | #8 Anaerobic Focus (Above targets) | #8 Anaerobic Focus (Above targets) |

TABLE 9-continued

TRAINING LOAD DISTRIBUTION FEEDBACK PHRASE LOGIC

| | Aer. High below minimal limit | Aer. High below target | Aer. High in target | Aer. High above target | Aer High above Very high limit |
|---|---|---|---|---|---|
| Aer. low above target | | | | | |
| Anaerobic below minimal limit | #3 Aer. high Shortage (#1 Below targets) | #4 Anaerobic shortage | #4 Anaerobic Shortage | #4 Anaerobic Shortage | #7 Aer. High Focus (Avove targets) |
| Anaerobic below target | #3 Aer. High Shortage | #6 Aer. Low Focus | #6 Aer. Low Focus | #5 Balanced | #7 Aer. High Focus (Above targets) |
| Anaerobic in target | #3 Aer. High Shortage | #6 Aer. Low Focus | #6 Aer. Low Focus | #5 Balanced | #7 Aer. High Focus (Above targets) |
| Anaerobic above target | #3 Aer. High Shortage | #6 Aer. Low Focus | #6 Aer. Low Focus | #2 Balanced (Above targets) | #7 Aer. High Focus (Above targets) |
| Anaerobic above very high limit | #3 Aer. High Shortage | #8 Anaerobic Focus | #8 Anaerobic Focus (Above targets) | #8 Anaerobic Focus (Above targets) | #8 Anaerobic Focus (Above targets) |
| Aer. low above very high limit | | | | | |
| Anaerobic below minimal limit | #3 Aer. High Shortage | #4 Anaerobic Shortage | #4 Anaerobic Shortage | #4 Anaerobic Shortage (Above targets) | #3 Aer. Low Focus (Above targets) |
| Anaerobic below target | #3 Aer. High Shortage | #6 Aer. Low Focus | #6 Aer. Low Focus (Above targets) | #6 Aer. Low Focus (Above targets) | #6 Aer. Low Focus (Above targets) |
| Anaerobic in target | #3 Aer. High Shortage | #6 Aer. Low Focus (Above targets) | #6 Aer. Low Focus (Above targets) | #6 Aer. Low Focus (Above targets) | #6 Aer. Low Focus (Above targets) |
| Anaerobic above target | #3 Aer. High Shortage | #6 Aer. Low Focus (Above targets) | #6 Aer. Low Focus (Above targets) | #6 Aer. Low Focus (Above targets) | #7 Aer. High Focus (Above targets) |
| Anaerobic abov every high limit | #3 Aer. High Shortage (Above targets) | #8 Anaerobic Focus (Above targets) | #8 Anaerobic Focus (Above targets) | #8 Anaerobic Focus (Above targets) | #8 Anaerobic Focus (Above targets) |

It may also be considered obvious for a person skilled in the art that the above presented 5×5×5 "decision cube" could be replaced with a more simple logic, for example using a 3×3×3 logic cube where each intensity category may be determined with 3-level scale: 1) below target 2) in target and 3) above target. The embodiment represented in the table above, including the 5-level scaling where each level may be as follows—1) below minimal limit 2) above minimal limit but below target 3) in target, 4) above target and 5) above very high limit—may enable more precise feedback while a more simple system may be easier to visualize in devices having small displays where additional limits may not fit that well to the device display.

Training Status Feedback Phrases

In an embodiment, combining different training load distribution feedback phrases with different training statuses enables more advanced, versatile feedback phrases than just a single training status. These advanced training status feedback may provide an explanation of the prevailing training status and may be beneficial for the planning of upcoming exercise sessions.

Within the THA analysis library, training_status_feedback_phrase interprets the current training status as it relates to the current training load distribution. For example, this may become useful if there is some element in the training load distribution that may explain current status. One example situation may be, for instance, if there is a poor training status (for example, unproductive), which may be explained by an unbalanced load distribution. Alternatively, there may be situations where training status is generally acceptable but there are improvements possible by adjusting the training load balance. Table 10 below shows the relationship between some example training statuses, similar to those described in applicant's earlier patent application US20180174685, as they relate to some training load distribution labels. Table 11 shows example feedback phrases corresponding to the logic number determined in Table 10.

TABLE 10

Training status feedback phrase logic.

| | #0<br>No result | #1<br>Below<br>Targets | #2<br>Aer. low<br>Shortage | #3<br>Aer. High<br>Shortage | #4<br>Anaerobic<br>Shortage | #5<br>Balanced | #6<br>Aer. Low<br>Focus |
|---|---|---|---|---|---|---|---|
| #0 No status | 0 | 1 | 2 | 3 | 4 | 5 | 6 |
| #1 Detraining | 10 | 11 | 12 | 13 | 14 | 15 | 16 |
| #2 Unproductive | 70 | 71 | 72 | 73 | 74 | 75 | 76 |
| #3 Overreaching | 60 | 61 | 62 | 63 | 64 | 65 | 66 |
| #4 Maintaining | 30 | 31 | 32 | 33 | 34 | 35 | 36 |
| #5 Recovery | 20 | 21 | 22 | 23 | 24 | 25 | 26 |
| #6 Peaking | 50 | 51 | 52 | 53 | 54 | 55 | 56 |
| #7 Productive | 40 | 41 | 42 | 43 | 44 | 45 | 46 |

| | #7<br>Aer. High<br>Focus | #8<br>Anaerobic<br>Focus | #9<br>Above Targets,<br>Aer. Low<br>Focus | #10<br>Above targets,<br>Aer. High<br>Focus | #11<br>Above targets,<br>Anaerobic<br>Focus | #12<br>Approaching<br>targets |
|---|---|---|---|---|---|---|
| #0 No status | 7 | 8 | 9 | 80 | 81 | 82 |
| #1 Detraining | 17 | 18 | 19 | 83 | 84 | 85 |
| #2 Unproductive | 77 | 78 | 79 | 101 | 102 | 103 |
| #3 Overreaching | 67 | 68 | 69 | 98 | 99 | 100 |
| #4 Maintaining | 37 | 38 | 39 | 89 | 90 | 91 |
| #5 Recovery | 27 | 28 | 29 | 86 | 87 | 88 |
| #6 Peaking | 57 | 58 | 59 | 95 | 96 | 97 |
| #7 Productive | 47 | 48 | 49 | 92 | 93 | 94 |

TABLE 11

Example feedback phrases based on relationship between training status and training distribution.

| Logic phrase number | Example feedback phrase |
|---|---|
| 0-9, 80-82 | "No status: Before we can determine your actual training status you typically need a few weeks of training history, including some activities with VO2max results from running or cycling." |
| 11-19, 83-85 | "Detraining - You've been training much less than recommended for a week or more, and it is starting to affect your fitness. Try increasing your training load to see improvement." |
| 22-24 | "Recovery - Your lighter training load is allowing your body to recover, which is essential during extended periods of hard training. When returning to higher training loads try to achieve better balance between different intensities." |
| 25-28 | "Recovery - Your lighter training load is allowing your body to recover, which is essential during extended periods of hard training. You can return to a higher training load when you feel ready." |
| 21, 88 | "Recovery - Although your lighter training load is allowing your body to recover, it is also contributing to your suboptimal monthly training load level. In long term, schedule only 1-2 easy training weeks for one month to keep monthly load at adequate level." |
| 29, 86, 87 | "Recovery - Your recently lowered training load is allowing for recovery, but your longer-term training load is still high." |
| 32-34 | "Maintaining - Your current training is enough to maintain your fitness level. Keep in mind that significant shortage in any training intensities typically causes suboptimal fitness development". |
| 35 | "Maintaining - Your current training is enough to maintain your fitness level. Keep in mind that by alternating easy and hard training weeks and training focus periodically might help you to increase your fitness level" |
| 36-38 | "Maintaining - During last month you have been focusing on a specific performance element but not seeing immediate results - that's sometimes the case so stay patient. after focusing long enough for a desired performance element try getting your distribution into balance" |
| 31, 91 | "Maintaining - Your current training is enough to maintain your fitness level. To see improvement try increasing total load to target." |
| 39, 89, 90 | "Maintaining - You have been training really hard. Remember to include easier training weeks into your schedule to ensure adequate recovery and supercompensation." |

TABLE 11-continued

Example feedback phrases based on relationship between training status and training distribution.

| Logic phrase number | Example feedback phrase |
|---|---|
| 42-44 | "Productive - Your fitness develops nicely . However, keep in mind that significant shortage in any training intensities causes suboptimal impulse for those specific physiological characteristics and increases monotony in terms of physiological training stimuli thus typically resulting in suboptimal fitness development". |
| 45-48 | "Productive - Good job! Your training distribution looks safe and sound and fitness develops nicely" |
| 41, 94 | "Productive - Your fitness seems to develop nicely despite low monthly training load. Try increasing overall load to targets to boost fitness development" |
| 49, 92, 93 | "Productive - You have been working really hard to get productive! Remember to include easier training weeks to ensure adequate recovery and fitness development in long term" |
| 52-54 | "Peaking - You are in ideal race condition! Your recently reduced training load is allowing your body to recover and fully compensate for earlier training. However, keep in mind that significant shortage in any training intensities causes suboptimal impulse for those specific physiological characteristics and increases monotony in terms of physiological training stimuli thus typically resulting in suboptimal fitness development". |
| 55-58 | "Peaking - You are in ideal race condition! Your recently reduced training load is allowing your body to recover and fully compensate for earlier training. Be sure to think ahead, since this peak state can only be maintained for a short time. |
| 51, 97 | "Peaking - Your performance seems to develop nicely! Although it seems that reduced training load is allowing your body to recover and fully compensate for earlier training - your past training has already been so easy that you can't keep up tapering for too long." |
| 59, 95, 96 | "Peaking - You are in ideal race condition! Your recently reduced training load is allowing your body to recover and fully compensate for earlier training. As your monthly training load is still high you can continue recovery period for a while". |
| 62, 67, 68 | "Overreaching - Your last week's training has been very hard and passed month's intensity training proportion is very high. Training has become counterproductive and your body needs a rest. When resuming your normal training focus some time on aerobic low intensity training |
| 63-66 | "Overreaching - Your weekly training load is very high and has become counterproductive. Your body needs a rest. Give yourself time to recover by adding lighter training to your schedule. |
| 61, 100 | "Overreaching - Your last week's training has been very hard. Training has become counterproductive and your body needs a rest. You can try approaching monthly targets a bit more slowly as this kind of overreaching periods should be done only occasionally. |
| 69, 98, 99 | "Overreaching - Both your weekly training load and monthly training load are very high and training has become counterproductive. Your body needs a rest. Give yourself time to recover by adding lighter training to your schedule. |
| 72 | "Unproductive - High relative amount of high intensity training may have turned your training status into Unproductive. Increase aerobic low intensity training to get Productive again" |
| 75-78 | "Unproductive - Your training seems OK but your fitness is decreasing. Your body may be struggling to recover, so be sure to pay attention to your overall health including stress, nutrition and rest." |
| 71 | "Unproductive - You should add your long term load. Your current training load does not seem to be sufficient to achieve fitness benefits" |
| 79, 101, 102 | "Unproductive - Your body may struggling to recover at the moment due to high monthly training load. You could try having an easier training period for a while." |
| 73 | "Unproductive - Insufficient amount of aerobic high intensity training may have caused a temporary reduction in performance. Try adding high intensity training to improve your Fitness level." |
| 74 | "Unproductive - Despite lack of anaerobic interval workouts your training seems otherwise OK. Your body may be struggling to recover, so be sure to pay attention to your overall health including stress, nutrition and rest." |

In one exemplary embodiment, feedbacks 10, 20, 30, 40, 50, 60 and 70 may never appear and thus do not receive a feedback phrase. These feedbacks do not appear since no other training load distribution feedbacks than #1-#12 are allowed when training status number is #1-#7.

As can be seen, the above matrix enables very detailed feedback. Alternatively, and as has been shown in some occasions the in above example table—feedback phrases in certain conditions can be combined which may be done to fit sentences to the comprehension level of target user level.

Figure 23:
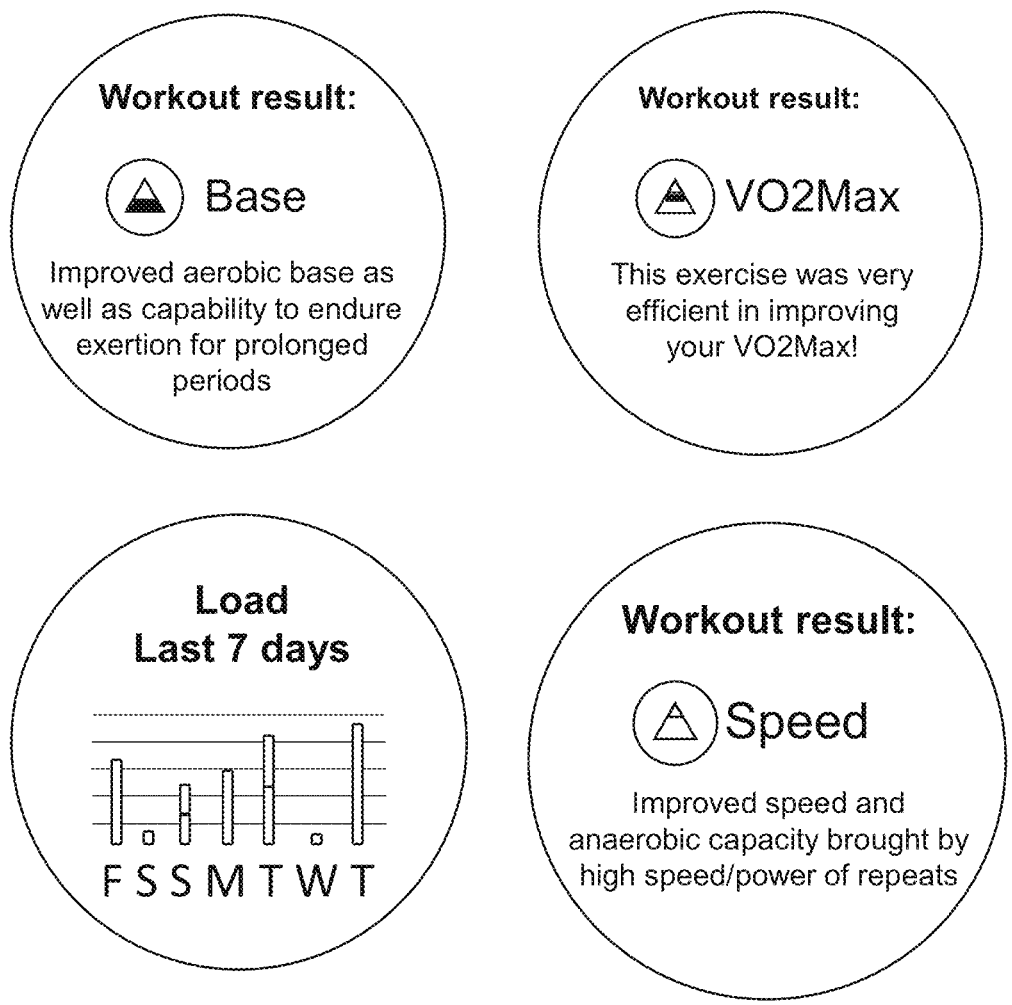

FIG. 23 displays an example user watch-style device user interface showing workout result label feedback. Workout labeling helps goal-oriented athletes to improve their performance by revealing the main impact brought by the workout:

- Each workout has different primary effect to fitness and physiological characteristics.
- Athletes know diverse training is necessary but hard to implement in practice due to lack of time and experience.
- Feature summarizes the main benefit/effect gained from exercise.

Figure 24:
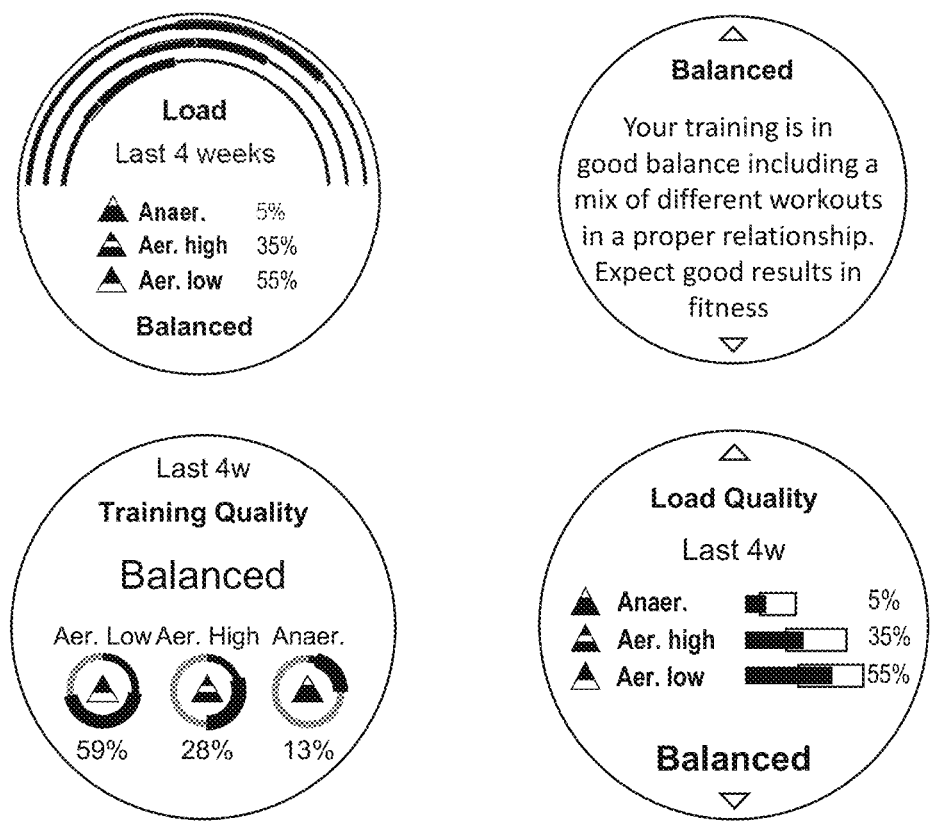
FIG. 24 displays an example watch-style device user interface showing multiple screens of training load balance feedback.

Categorizes the quality of the workout to main three areas of fitness, used in coaching (base/capacity/power)
Based on EPOC, TRIMP and recognized areas of physiological impact FIG. 24 displays an example watch-style device user interface showing multiple screens of training load balance feedback. It shows training load balance as calculated training history analysis (THA) library outputs:
1. Sum of Training Load for past 4 w for each category (Aer. low, Aer. high, Anaerobic)
2. Upper and lower training load limits for target 4 w Training Load for each category
3. Feedback phrase number for Training Load Balance interpretation
4. % distribution to calculate based on Training Load sum values ETE real-time library will be updated to output Workout Label to be inputted into THA The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for determining a training load distribution of a user using a device with a processor, memory and software, the method comprising:
determining and storing a value depicting a fitness level of user and a value depicting a maximum heart rate of the user;
continuously measuring heart rate by a heart sensor and recording selected number of measured values;
obtaining intensity values depicting exercise intensity, alternatively by calculating continuously an exercise intensity using a measured heart rate value and recording selected number of calculated intensity values and/or by measuring, external workload;
calculating an aerobic training load and an aerobic training effect using said intensity values;
determining, each high intensity period from the recorded values of exercise intensity values and determining characteristics of an interval including:
at least one derivative of intensity; and
at least one of:
an amount of intensity increase during the high intensity period;
a duration of the high intensity period; and
an external workload during the high intensity period;
calculating an anaerobic training load and an anaerobic training effect using the determined characteristics;
dividing the aerobic training effect into intensity categories of: Aerobic Low and Aerobic High, based on a cumulative time at predetermined zones of speed, average power and/or heart rate each scaled based on the fitness level, and dependent on the calculated anaerobic training effect and the calculated aerobic training effect, wherein an activity class (AC)-based target values for monthly training load (MTL) are determined for each intensity category;
storing the calculated training load into three intensity categories of Aerobic Low, Aerobic High and Anaerobic, in order to provide a training load distribution between the three intensity categories; and
outputting the training load distribution to an output device;
wherein the category Aerobic High involves a higher heart rate than the category Aerobic Low and does not belong in the category of Anaerobic.

2. The method according to claim 1, wherein one or more of the intensity categories are further divided into subcategories.

3. The method according to claim 2, wherein
the Aerobic Low category is further divided into sub-categories of Recovery and Base; and/or
the Aerobic High category is dived into two or more sub-categories of Tempo, Lactate threshold and VO2 max; and/or
the Anaerobic category is divided into Anaerobic capacity and speed.

4. The method according to claim 1, comprising classifying a workout into two or more categories is based on the aerobic training effect, anaerobic training effect and time spent at different intensity zones during the workout, wherein the categories depict the physiological benefit of the workout.

5. The method according to the claim 1, wherein
the intensity is measured as a relative intensity,
wherein the relative intensity is benchmarked against one or more of: lactate threshold heart rate (LTHR), lactate threshold speed (LT speed), functional threshold power (FTP), VO2 max and speed/power corresponding to VO2 max of the user.

6. The method according to claim 1, wherein the distributed training load comprises summing all of the accumulated training loads of each intensity category.

7. The method according to the claim 1, wherein the training effect is a scaled value of a training load, which is measurable using cumulative scores of excess post-exercise oxygen consumption (EPOC) or training impulse (TRIMP).

8. The method according to claim 1, wherein the training load distribution is outputted as a daily calendar, a weekly (7-day) illustration, a monthly (28-day) illustration, a custom date as specified by the user, or a yearly (365-day) distribution.

9. The method according to claim 1, wherein the category Aerobic Low corresponds to a low-intensity aerobic training, optionally an aerobic exercise at a heart rate below 90% of the user's lactate threshold heart rate (LTHR).

10. The method according to claim 1, comprising calculating the training load sums for each intensity category and the training load target areas for each intensity category.

11. The method according to claim 1, comprising an activity class (AC) of the user, which refers to the user's fitness level, activity history or training history; and evaluating the present activity class (AC) using background information, a fitness level, a maximum oxygen consumption value and/or training history data; and wherein each activity class (AC) has its own specific training load target, which preferably comprises a range, more preferably the training load target comprises a lowest limit for a training load of the activity class (AC) and an upper limit for a training load of the activity class (AC).

12. The method according to claim 11, comprising an average activity class (AC), which is a maximum of a VO2 max-based value, a monthly (28-day) training load-based value, and an activity class constant, wherein the monthly training load is calculated as a weighted sum, optionally the monthly training sum is calculated by computing the daily average training load of the user as a weighted average, and scaling the daily average training load to an average monthly training load.

13. The method according the claim 1, comprising
- determining primary and secondary benefits of exercise using said aerobic training effect, anaerobic training effect and time at different intensity zones, wherein the primary and secondary benefits are selected from a group of: Recovery, Base, Tempo, Lactate Threshold, VO2 max, Anaerobic capacity and speed; and
- determining magnitude of the primary and secondary benefits based on the accumulated aerobic load and the accumulated anaerobic load.

14. The method according to claim 1, wherein the high intensity intervals are detected by analyzing the derivatives of heart rate with regard to time, i.e. the degree of heart rate changes.

15. The method according to claim 1, comprising providing guidance based on the sums of the aerobic and anaerobic loads, and respective personal targets, said targets being based on the fitness level and total accumulated training load in history.

16. The method according to claim 1, wherein the characteristics of each interval comprises at least:
- starting % HRmax or % VO2 max-value,
- final peak % HRmax or % VO2 max-value, and
- a value depicting the end of the interval,
- and timestamps of the characteristics.

* * * * *